US009644204B2

(12) United States Patent
Hindson et al.

(10) Patent No.: US 9,644,204 B2
(45) Date of Patent: May 9, 2017

(54) PARTITIONING AND PROCESSING OF ANALYTES AND OTHER SPECIES

(71) Applicant: 10X Genomics, Inc., Pleasanton, CA (US)

(72) Inventors: Benjamin Hindson, Pleasanton, CA (US); Serge Saxonov, Oakland, CA (US); Kevin Ness, Pleasanton, CA (US); Paul Hardenbol, San Francisco, CA (US); Christopher Hindson, Pleasanton, CA (US); Donald Masquelier, Tracy, CA (US); Mirna Jarosz, Palo Alto, CA (US); Michael Schnall-Levin, Palo Alto, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 61 days.

(21) Appl. No.: 14/175,935

(22) Filed: Feb. 7, 2014

(65) Prior Publication Data

US 2014/0227684 A1 Aug. 14, 2014

Related U.S. Application Data

(60) Provisional application No. 61/762,435, filed on Feb. 8, 2013, provisional application No. 61/800,223, filed on Mar. 15, 2013, provisional application No. 61/840,403, filed on Jun. 27, 2013, provisional application No. 61/844,804, filed on Jul. 10, 2013.

(51) Int. Cl.
*C12Q 1/68* (2006.01)
*C07H 21/00* (2006.01)
*C12P 19/34* (2006.01)
*G01N 33/50* (2006.01)
*C12N 15/10* (2006.01)
*C12N 15/11* (2006.01)
*G01N 33/543* (2006.01)

(52) U.S. Cl.
CPC ......... *C12N 15/1065* (2013.01); *C12N 15/11* (2013.01); *C12Q 1/6806* (2013.01); *C12Q 1/6874* (2013.01); *C12Q 1/6876* (2013.01); *G01N 33/5436* (2013.01); *C12Q 2600/112* (2013.01)

(58) Field of Classification Search
CPC ......... C12Q 1/68; C12Q 1/6806; G01N 33/50
See application file for complete search history.

(56) References Cited

U.S. PATENT DOCUMENTS

| 4,582,802 A | 4/1986 | Zimmerman et al. |
| 5,149,625 A | 9/1992 | Church et al. |
| 5,202,231 A | 4/1993 | Drmanac et al. |
| 5,413,924 A | 5/1995 | Kozak et al. |
| 5,436,130 A | 7/1995 | Mathies et al. |
| 5,512,131 A | 4/1996 | Kumar et al. |
| 5,587,128 A | 12/1996 | Wilding et al. |
| 5,605,793 A * | 2/1997 | Stemmer .......... C07K 14/43595 435/6.11 |
| 5,618,711 A | 4/1997 | Gelfand et al. |
| 5,695,940 A | 12/1997 | Drmanac et al. |
| 5,736,330 A | 4/1998 | Fulton |
| 5,756,334 A | 5/1998 | Perler et al. |
| 5,834,197 A | 11/1998 | Parton |
| 5,851,769 A | 12/1998 | Gray et al. |
| 5,856,174 A | 1/1999 | Lipshutz et al. |
| 5,958,703 A | 9/1999 | Dower et al. |
| 5,994,056 A | 11/1999 | Higuchi |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,143,496 A | 11/2000 | Brown et al. |
| 6,172,218 B1 | 1/2001 | Brenner |
| 6,265,552 B1 | 7/2001 | Schatz |
| 6,297,006 B1 | 10/2001 | Drmanac et al. |
| 6,297,017 B1 | 10/2001 | Schmidt et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |

(Continued)

FOREIGN PATENT DOCUMENTS

| EP | 0249007 A2 | 12/1987 |
| EP | 0271281 A2 | 6/1988 |

(Continued)

OTHER PUBLICATIONS

Makino et al., Colloids and Surfaces B : Biointerfaces 12 :97 (1998).*
Nagashima et al.,Colloids and Surfaces B : Biointerfaces 12 :97 (1998).*
Office action dated Oct. 9, 2015 for U.S. Appl. No. 14/680,808.
U.S. Appl. No. 13/966,150, filed Aug. 13, 2013, Hindson et al.
U.S. Appl. No. 14/104,650, filed Dec. 12, 2013, Hindson et al.
U.S. Appl. No. 14/175,973, filed Feb. 7, 2014, Hindson et al.
Abate et al., Valve-based flow focusing for drog formation. Appl Phys Left. 2009;94. 3 pages.

(Continued)

*Primary Examiner* — Ethan C Whisenant
(74) *Attorney, Agent, or Firm* — Wilson Sonsini Goodrich & Rosati

(57) ABSTRACT

The present disclosure provides compositions, methods, systems, and devices for polynucleotide processing. Such polynucleotide processing may be useful for a variety of applications, including polynucleotide sequencing.

40 Claims, 16 Drawing Sheets

(56) References Cited

U.S. PATENT DOCUMENTS

| | | |
|---|---|---|
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,297,485 B2 | 11/2007 | Bornarth et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac et al. |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,053,192 B2 | 11/2011 | Bignell et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,986,286 B2 | 3/2015 | Tanghoj et al. |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,249,460 B2 | 2/2016 | Pushkarev et al. |
| 9,347,059 B2 | 5/2016 | Saxonov |
| 9,388,465 B2 | 7/2016 | Hindson et al. |
| 9,410,201 B2 | 8/2016 | Hindson et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027221 A1* | 2/2003 | Scott ................ C12Q 1/68 435/7.21 |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0082587 A1 | 5/2003 | Seul et al. |
| 2003/0104466 A1 | 6/2003 | Knapp et al. |
| 2003/0108897 A1 | 6/2003 | Drmanac |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1* | 11/2003 | Trnovsky ............ C12Q 1/68 435/5 |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1* | 12/2004 | Dominowski ........ A61K 9/1075 424/184.1 |
| 2005/0019839 A1 | 1/2005 | Jesperson et al. |
| 2005/0042625 A1 | 2/2005 | Schmidt et al. |
| 2005/0079510 A1* | 4/2005 | Berka ............... B01L 3/502707 506/16 |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1* | 9/2005 | Trau ..................... B01J 13/02 435/6.16 |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0002890 A1 | 1/2006 | Hersel et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1* | 8/2007 | Livak ................ C12Q 1/6816 435/6.19 |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2009/0005252 A1 | 1/2009 | Drmanac et al. |
| 2009/0011943 A1 | 1/2009 | Drmanac et al. |
| 2009/0012187 A1* | 1/2009 | Chu ..................... A61K 9/113 516/54 |
| 2009/0025277 A1* | 1/2009 | Takanashi ............ C10G 31/08 44/302 |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |

(56) References Cited

U.S. PATENT DOCUMENTS

| | | |
|---|---|---|
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0309002 A1 | 12/2012 | Link |
| 2012/0316074 A1 | 12/2012 | Saxonov |
| 2013/0018970 A1 | 1/2013 | Woundy et al. |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1* | 7/2013 | So .................. G01N 1/34 435/6.12 |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227706 A1* | 8/2014 | Kato .................. C12Q 1/6886 435/6.12 |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0111256 A1* | 4/2015 | Church .................. C12Q 1/6851 435/91.2 |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0122817 A1 | 5/2016 | Jarosz et al. |
| 2016/0244742 A1 | 8/2016 | Linnarsson et al. |
| 2016/0257984 A1 | 9/2016 | Hardenbol et al. |
| 2016/0304860 A1 | 10/2016 | Hindson et al. |

FOREIGN PATENT DOCUMENTS

| | | |
|---|---|---|
| EP | 0637996 B1 | 7/1997 |
| EP | 1019496 B1 | 9/2004 |
| EP | 1482036 B1 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| GB | 2485850 A | 5/2012 |
| JP | S 5949832 A | 3/1984 |
| JP | 2006-507921 A | 3/2006 |
| JP | 2006-289250 A | 10/2006 |
| JP | 2007-268350 A | 10/2007 |
| JP | 2009-208074 A | 9/2009 |
| WO | WO-9530782 A1 | 11/1995 |
| WO | WO 96/29629 A2 | 3/1996 |
| WO | WO 96/41011 A1 | 12/1996 |
| WO | WO 99/09217 A1 | 2/1999 |
| WO | WO 99/52708 A1 | 10/1999 |
| WO | WO 00/08212 A1 | 2/2000 |
| WO | WO 00/26412 A1 | 5/2000 |
| WO | WO-0070095 A2 | 11/2000 |
| WO | WO 01/14589 A2 | 3/2001 |
| WO | WO 01/89787 A2 | 11/2001 |
| WO | WO 02/31203 A2 | 4/2002 |
| WO | WO 02/086148 A1 | 10/2002 |
| WO | WO 2004/002627 A2 | 1/2004 |
| WO | WO 2004/010106 A2 | 1/2004 |
| WO | WO-2004069849 A2 | 8/2004 |
| WO | WO 2004/091763 A2 | 10/2004 |

(56) References Cited

FOREIGN PATENT DOCUMENTS

| | | |
|---|---|---|
| WO | WO 2004/102204 A1 | 11/2004 |
| WO | WO 2004/103565 A2 | 12/2004 |
| WO | WO 2004/105734 A1 | 12/2004 |
| WO | WO-2005002730 A1 | 1/2005 |
| WO | WO 2005/082098 A2 | 2/2005 |
| WO | WO 2005/021151 A1 | 3/2005 |
| WO | WO 2005/023331 A2 | 3/2005 |
| WO | WO 2005/040406 A1 | 5/2005 |
| WO | WO 2005/049787 A2 | 6/2005 |
| WO | WO 2006/030993 A1 | 3/2006 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/091792 A2 | 1/2008 |
| WO | WO 2008/021123 A1 | 2/2008 |
| WO | WO 2008/102057 A1 | 8/2008 |
| WO | WO 2008/109176 A2 | 9/2008 |
| WO | WO 2008/121342 A2 | 10/2008 |
| WO | WO 2008/134153 A1 | 11/2008 |
| WO | WO 2009/005680 A1 | 1/2009 |
| WO | WO 2009/011808 A1 | 1/2009 |
| WO | WO 2009/061372 A1 | 5/2009 |
| WO | WO 2009/085215 A1 | 7/2009 |
| WO | WO 2010/004018 A1 | 1/2010 |
| WO | WO 2010/033200 A2 | 3/2010 |
| WO | WO-2010115154 A1 | 10/2010 |
| WO | WO 2010/148039 A2 | 12/2010 |
| WO | WO 2010/151776 A2 | 12/2010 |
| WO | WO 2011/047870 A1 | 4/2011 |
| WO | WO 2011/056546 A1 | 5/2011 |
| WO | WO 2011/066476 A1 | 6/2011 |
| WO | WO-2011074960 A1 | 6/2011 |
| WO | WO 2012/012037 A1 | 1/2012 |
| WO | WO 2012/048341 A1 | 4/2012 |
| WO | WO 2012/083225 A2 | 6/2012 |
| WO | WO-2012106546 A2 | 8/2012 |
| WO | WO-2012112970 A2 | 8/2012 |
| WO | WO-2012142611 A2 | 10/2012 |
| WO | WO 2012/149042 A2 | 11/2012 |
| WO | WO 2012/166425 A2 | 12/2012 |
| WO | WO-2013019751 A1 | 2/2013 |
| WO | WO-2013036929 A1 | 3/2013 |
| WO | WO-2013122996 A1 | 8/2013 |
| WO | WO-2013123125 A1 | 8/2013 |
| WO | WO 2013/177220 A1 | 11/2013 |
| WO | WO 2014/028537 A1 | 2/2014 |
| WO | WO-2014074611 A1 | 5/2014 |
| WO | WO-2014093676 A1 | 6/2014 |
| WO | WO-2014210353 A2 | 12/2014 |
| WO | WO-2015044428 A1 | 4/2015 |
| WO | WO-2015164212 A1 | 10/2015 |

OTHER PUBLICATIONS

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Advisory Action mailed Nov. 20, 2013 for U.S. Appl. No. 13/139,326.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Anna et al., "Formation of dispersions using 'flow focusing' in microchannels", Appln. Phys. Letts. 82:3 364 (2003).
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Carroll, "The selection of high-producing cell lines using flow cytometry and cell sorting", Exp. Op. Bioi. Therp., 4:11 1821-1829 (2004).
Chaudhary "A rapid method of cloning functioNal variable-region antibody genese in *Escherichia coli* as single-chain immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chinese Office Action and search report mailed May 23, 2013 for Application No. CN 200880127116.4.
Chinese office action dated Jun. 18, 2012 for CN Application No. 200880127116.4.
Clausell-Tormos et al., "Droplet-based microfluidic platforms for the encapsulation and screening of mammalian cells and multicellular organisms", Chem. Biol. 15:427-437 (2008).
De Bruin et al., UBS Investment Research. Q-Series®: DNa Sequencing. UBS Securities LLC. Jul. 12, 2007. 15 pages.
Demirci, et al. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Dowding, et al. Oil core/polymer shell microcapsules by interNal phase separation from emulsion droplets. II: controlling the release profile of active molecules. Langmuir. Jun. 7, 2005;21(12):5278-84.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Esser-Kahn, et al. Triggered release from polymer capsules. Macromolecules. 2011; 44:5539-5553.
European office action dated Jan. 23, 2012 for Application No. EP 08865992.5.
European office action dated Apr. 5, 2013 for Application No. EP 08865992.5.
European office action dated Aug. 29, 2013 for Application No. EP 08865992.5.
European office action dated Dec. 15, 2010 for EP Application No. 08865992.5.
Freiberg, et al. Polymer microspheres for controlled drug release. Int J Pharm. Sep. 10, 2004;282(1-2):1-18.
Fu, "A micro fabricated fluorescence-activated cell sorter", Nature Biotech., 17:1109-1111 (1997).
Fulton et al., Advanced multiplexed analysis with the FlowMetrix system. Clin Chern. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Hashimshony, et al. CEL-Seq: Single-Cell RNa-Seq by Multiplexed Linear Amplification. Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" ANal. Chern 77: 1539-1544 (2005).
Holtze, et al. Biocompatible surfactants for water-in-fluorocarbon emulsions. Lab Chip. Oct. 2008;8(10):1632-9. doi: 10.1039/b806706f. Epub Sep. 2, 2008.

(56) References Cited

OTHER PUBLICATIONS

Huebner, "Quantitative detection of protein expression in single cells using droplet microfluidics", Chem. Commun 1218-1220 (2007).
International Preliminary Report on Patentability dated Mar. 31, 2011 for PCT/US09/005184.
International Preliminary Report on Patentability dated May 10, 2012 for PCT/US2010/054050.
International Preliminary Report on Patentability dated Jun. 30, 2011 for PCT/US2009/006649.
International Preliminary Report on Patentability dated Jul. 1, 2010 for PCT/US2008/013912.
International Preliminary Report on Patentability dated Sep. 17, 2009 for PCT/US2008/003185 mailed Sep. 17, 2009.
International search report and written opinion dated Jan. 12, 2009 for PCT/US2008/003185.
International search report and written opinion dated Jan. 31, 2011 for PCT/US2010/054050.
International search report and written opinion dated Apr. 3, 2009 for PCT/US2008/013912.
International search report and written opinion dated Aug. 16, 2010 for PCT/US2009/005184.
International search report and written opinion dated Oct. 2, 2009 for PCT/US2009/004037.
International search report and written opinion dated Oct. 21, 2009 for PCT/US2009/003389.
International search report and written opinion dated Oct. 29, 2008 for PCT/US2008/008563.
International search report and written opinion dated Dec. 16, 2013 for PCT/US2013/054797.
International search report dated Apr. 22, 2009 for PCT/US2009/000664.
Japanese Office Action and mailed Jul. 17, 2013 for Application No. JP 2010-539498.
Japanese Office Action mailed Nov. 19, 2013 for Application No. JP 2012-536941.
Khomiakov A et al., [Analysis of perfect and mismatched DNA duplexes by a generic hexanucleotide microchip]. Mol Bioi (Mosk). Jul.-Aug. 2003;37(4):726-41. Russian. Abstract only.
Kim, et al. Albumin loaded microsphere of amphiphilic poly(ethylene glycol)/poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Koster et al., "Drop-based microfluidic devices for encapsulation of single cells", Lab on a Chip the Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Li, Y., et al., "PEGylated PLGA Nanoparticles as protein carriers: synthesis, preparation and biodistribution in rats," JourNal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Marcus. Gene method offers diagnostic hope. The Wall Street JourNal. Jul. 11, 2012.
Merriman, et al. Progress in ion torrent semiconductor chip based sequencing. Electrophoresis. Dec. 2012;33(23):3397-417. doi: 10.1002/elps.201200424.
Mirzabekov, "DNA Sequencing by Hybridization—a Megasequencing Method and a Diagnostic Tool?" Trends in Biotechnology 12(1): 27-32 (1994).
Mouritzen et al., Single nucleotide polymorphism genotyping using locked nucleic acid (LNa). Expert Rev Mol Diagn. Jan. 2003;3(1):27-38.
Nguyen, et al. In situ hybridization to chromosomes stabilized in gel microdrops. Cytometry. 1995; 21:111-119.
Oberholzer, et al. Polymerase chain reaction in liposomes. Chem Biol. Oct. 1995;2(10):677-82.
Office action dated Jan. 4, 2010 for U.S. Appl. No. 12/172,186.
Office action dated Feb. 28, 2013 for U.S. Appl. No. 13/139,326.
Office action dated Apr. 24, 2013 for U.S. Appl. No. 13/119,470.
Office action dated Aug. 6, 2013 for U.S. Appl. No. 13/139,326.
Office action dated Sep. 17, 2013 for U.S. Appl. No. 13/503,588.
Ogawa, et al. Production and characterization of O/W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," JourNal of Controlled Release, vol. 75, pp. 211-224 (2001).
Peters, et al. Accurate whole-genome sequencing and haplotyping from 10 to 20 human cells. Nature. Jul. 11, 2012;487(7406):190-5. doi: 10.1038/Nature11236.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: aNalysis of the NFI gene. Genet Test. 2006 Spring;10(1):8-17.
Schmitt, "Bead-based multiplex genotyping of human papillomaviruses", J. Clinical Microbial., 44:2 504-512 (2006).
Shah, "Fabrication of mono disperse thermosensitive microgels and gel capsules in micro fluidic devices", Soft Matter, 4:2303-2309 (2008).
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., DiscrimiNation between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese JourNal Experimental Surgery. May 2005;22(5):639-40.
Theberge, et al. Microdropelts in microfluidics: an evolving platform for discoveries in chemsitry and biology. Angew Chem Int Ed Engl. Aug. 9, 2010;49(34):5846-68. doi: 10.1002/anie.200906653.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Wang et al., Single nucleotide polymorphism discrimiNation assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Weaver, "Rapid clonal growth measurements at the single-cell level: gel microdroplets and flow cytometry", Biotechnology, 9:873-877 (1991).

(56) References Cited

OTHER PUBLICATIONS

Whitesides, "Soft lithography in biology and biochemistry", Annual Review of Biomedical Engineering, 3:335-373 (2001).
Williams, et al. Amplification of complex gene libraries by emulsion PCR. Nat Methods. Jul. 2006;3(7):545-50.
Woo, et al. G/C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)/EDTA-base artificial restriction DNa cutter for versatile manipulation of doulbe-stranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021/bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zimmermann et at., Microscale production of hybridomas by hypo-osmolar electrofusion. Hum• Antibodies Hybridomas. Jan. 1992;3(1): 14-8.
Zong, et al. Genome-wide detection of single-nucleotide and copy-No. variations of a single human cell. Science. Dec. 21, 2012;338(6114):1622-6. doi: 10.1126/science.1229164.
U.S. Appl. No. 14/316,383, filed Jun. 26, 2014, Hindson et al.
U.S. Appl. No. 14/316,398, filed Jun. 26, 2014, Hindson et al.
U.S. Appl. No. 14/316,416, filed Jun. 26, 2014, Hindson et al.
U.S. Appl. No. 14/316,431, filed Jun. 26, 2014, Hindson et al.
U.S. Appl. No. 14/316,447, filed Jun. 26, 2014, Hindson et al.
U.S. Appl. No. 14/316,463, filed Jun. 26, 2014, Hindson et al.
Advisory Action dated Mar. 21, 2014 for U.S. Appl. No. 13/119,470.
Advisory Action dated May 16, 2014 for U.S. Appl. No. 13/503,588.
Australian Office Action issued Dec. 17, 2013 for Application No. AU 2010315580.
Boone, et al. Plastic advances microfluidic devices. The devices debuted in silicon and glass, but plastic fabrication may make them hugely successful in biotechnology application. Analytical Chemistry. Feb. 2002; 78A-86A.
Fisher, et al. A scalable, fully automated process for construction of sequence-ready human exome targeted capture libraries. Genome Biol. 2011;12(1):R1. doi: 10.1186/gb-2011-12-1-rl. Epub Jan. 4, 2011.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy, et al. Directed evolution of polymerase function by compartmentalized self-replication. Proc Natl Acad Sci U S A. Apr. 10, 2001;98(8):4552-7. Epub Mar. 27, 2001.
International search report and written opinion dated May 14, 2014 for PCT/US2014/015427.
International search report and written opinion dated May 16, 2014 for PCT/US2013/074764.
Japanese Final Rejection dated Aug. 5, 2014 for Application No. JP 2012-536941.
Microfluidic ChipShop. Microfluidic product catalogue. Mar. 2005.
Microfluidic ChipShop. Microfluidic product catalogue. Oct. 2009.
Notice of Allowance dated Jan. 27, 2014 for U.S. Appl. No. 13/139,326.
Office action dated Feb. 10, 2014 for U.S. Appl. No. 13/503,588.
Office action dated May 20, 2014 for U.S. Appl. No. 14/172,266.
Office action dated May 20, 2014 for U.S. Appl. No. 14/172,326.
Office action dated May 28, 2013 for U.S. Appl. No. 12/529,926.
Office action dated Jul. 30, 2014 for U.S. Appl. No. 12/809,120.
Office action dated Aug. 6, 2014 for U.S. Appl. No. 12/529,926.
Office action dated Oct. 1, 2012 for U.S. Appl. No. 12/529,926.
Office action dated Dec. 5, 2013 for U.S. Appl. No. 13/119,470.
Office Action mailed Apr. 29, 2014 for EP Application No. 08865992.5.
Office Action mailed Dec. 16, 2013 for CN Application No. 201080055990.9.
Office Action mailed May 23, 2013 for CN Application No. 200880127116.4.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Hug, et al. Measurement of the Number of molecules of a single mRNA species in a complex mRNA preparation. J Theor Biol. Apr. 21, 2003;221(4):615-24.
Office action dated Sep. 10, 2014 for U.S. Appl. No. 14/250,701.
U.S. Appl. No. 14/680,808, filed Apr. 7, 2015, Hindson et al.
Gyarmati, et al. Reversible disulphide formation in polymer networks: a versatile functional group from synthesis to applications. European Polymer Journal. 2013; 49:1268-1286.
Office action dated Apr. 20, 2015 for U.S. Appl. No. 13/966,150.
U.S. Appl. No. 14/682,952, filed Apr. 8, 2015, Bharadwaj et al.
International search report and written opinion dated May 14, 2015 for PCT/US2014/044398.
Chou, et al. Disposable Microdevices for DNA Analysis and Cell Sorting. Proc. Solid-State Sensor and Actuator Workshop, Hilton Head, SC. Jun. 8-11, 1998; 11-14.
Tawfik, et al. Man-made cell-like compartments for molecular evolution. Nat Biotechnol. Jul. 1998;16(7):652-6.
Office action dated Sep. 16, 2015 for U.S. Appl. No. 14/175,973.
International search report and written opinion dated Aug. 19, 2015 for PCT/US2015/025197.
U.S. Appl. No. 14/624,468, filed Feb. 17, 2015, Hindson et al.
U.S. Appl. No. 14/624,473, filed Feb. 17, 2015, Hindson et al.
U.S. Appl. No. 14/624,484, filed Feb. 17, 2015, Hindson et al.
Office action dated Jan. 15, 2015 for U.S. Appl. No. 14/250,701.
European search report and opinion dated Feb. 2, 2016 for EP Application No. 13829413.
Office action dated Feb. 23, 2016 for U.S. Appl. No. 14/104,650.
Office action dated Mar. 1, 2016 for U.S. Appl. No. 14/250,701.
Office action dated Mar. 4, 2016 for U.S. Appl. No. 14/175,973.
Office action dated Mar. 14, 2016 for U.S. Appl. No. 14/680,808.
Shimkus, et al. A chemically cleavable biotinylated nucleotide: usefulness in the recovery of protein-DNA complexes from avidin affinity columns Proc Natl Acad Sci U S A. May 1985;82(9):2593-7.
Office action dated Jun. 23, 2016 for U.S. Appl. No. 14/624,473.
Office action dated Jun. 24, 2016 for U.S. Appl. No. 14/624,468.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Attia, et al. Micro-injection moulding of polymer microfluidic devices. Microfluidics and Nanofluidics. 2009; 7(1):1-28.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chu, et al. Controllable monodisperse multiple emulsions. Angew Chem Int Ed Engl. 2007;46(47):8970-4.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.

(56) References Cited

OTHER PUBLICATIONS

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
European search report and opinion dated Jul. 25, 2016 for EP Application No. 13862194.1.
European search report and opinion dated Jul. 25, 2016 for EP Application No. 14748569.2.
European search report and opinion dated Jul. 25, 2016 for EP Application No. 14817610.
European search report and opinion dated Jul. 26, 2016 for EP Application No. 14749595.6.
Fredrickson, et al. Macro-to-micro interfaces for microfluidic devices. Lab Chip. Dec. 2004;4(6):526-33. Epub Nov. 10, 2004.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Klein, et al. Droplet barcoding for single-cell transcriptomics applied to embryonic stem cells. Cell. May 21, 2015;161(5):1187-201. doi: 10.1016/j.cell.2015.04.044.
Lagus, et al. A review of the theory, methods and recent applications of high-throughput single-cell droplet microfluidics. J. Phys. D: Appl. Phys. (2013) 46:114005. (21 pages).
Lowe, Adam J. Norbornenes and [n]polynorbornanes as molecular scaffolds for anion recognition. Ph.D. Thesis (May 2010). (361 pages).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Moore, et al. Behavior of capillary valves in centrifugal microfluidic devices prepared by three-dimensional printing. Microfluidics and Nanofluidics. 2011; 10(4):877-888.
Navin. The first five years of single-cell cancer genomics and beyond. Genome Res. Oct. 2015;25(10):1499-507. doi: 10.1101/gr.191098.115.
Novak, et al. Single cell multiplex gene detection and sequencing using microfluidically generated agarose emulsions. Angew Chem Int Ed Engl. Jan. 10, 2011;50(2):390-5. doi: 10.1002/anie.201006080.
Office action dated Aug. 11, 2016 for U.S. Appl. No. 14/250,701.
Office action dated Sep. 15, 2016 for U.S. Appl. No. 15/200,928.
Office action dated Oct. 12, 2016 for U.S. Appl. No. 14/316,447.
Office action dated Nov. 8, 2016 for U.S. Appl. No. 13/966,150.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Seiffert, et al. Smart microgel capsules from macromolecular precursors. J Am Chem Soc. May 12, 2010;132(18):6606-9. doi: 10.1021/ja102156h.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Tonelli, et al. Perfluoropolyether functional oligomers: unusual reactivity in organic chemistry. Journal of Fluorine Chemistry. 2002; 118(1)"107-121.
Turner, et al. Methods for genomic partitioning. Annu Rev Genomics Hum Genet. 2009;10:263-84. doi: 10.1146/annurev-genom-082908-150112. Review.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Office action dated Nov. 6, 2015 for U.S. Appl. No. 13/966,150.
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Bodi, K. et al. "Comparison of Commercially Available Target Enrichment Methods for Next-Generation Sequencing" J Biomolecular Techniques (2013) 24:73-86.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Coufal, et al. L1 retrotransposition in human neural progenitor cells. Nature. Aug. 27, 2009;460(7259):1127-31. doi: 10.1038/nature08248. Epub Aug. 5, 2009.
Doshi, et al. Red blood cell-mimicking synthetic biomaterial particles. Proceedings of the National Academy of Sciences 106.51 (2009): 21495-21499.
Fan, et al. Noninvasive diagnosis of fetal aneuploidy by shotgun sequencing DNA from maternal blood. Proc Natl Acad Sci U S A. Oct. 21, 2008;105(42)16266-71. doi: 10.1073/pnas.0808319105. Epub Oct. 6, 2008.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fu, A.Y., et al., "A microfabricated fluorescence-activated cell sorter," Nature Biotechnology, vol. 17, pp. 1109-1111 (1999).
Gericke, et al. Functional cellulose beads: preparation, characterization, and applications. Chemical reviews 113.7 (2013): 4812-4836.
He, J. et al. "Genotyping-by-sequencing (GBS), an ultimate marker-assisted selections (MAS) tool to accelerate plant breeding" Frontiers in Plant Sci (Sep. 30, 2014) 5:1-8.

(56) References Cited

OTHER PUBLICATIONS

Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.

Ioannidis, N. Manufacturing of Agarose-Based Chromatographic Adsorbents With Controlled Pore and Particle Sizes. A thesis submitted to the University of Birmingham for the degree of Doctor of Philosophy. 2009.

Lee, J-H. et al. "Fluorescent in situ sequencing (FISSEQ) of RNA for gene expression profiling in intact cells and tissues" Nature Protocols (Feb. 12, 2015) 10(3):442-458.

Morgan, et al. Chapter 12: Human microbiome analysis. PLoS Comput Biol. 2012;8(12):e1002808. doi: 10.1371/journal.pcbi.1002808. Epub Dec. 27, 2012.

Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_nin_english.pdf.

Muotri, et al. L1 retrotransposition in neurons is modulated by MeCP2. Nature. Nov. 18, 2010;468(7322):443-6. doi: 10.1038/nature09544.

Oligotex Handbook. For purification of poly A+RNA from total RNA and directly from cultured cells or tissues as well as purification of polyadenylated in vitro transcripts. Jun. 2012.

Pantel, et al. Detection methods of circulating tumor cells. J Thorac Dis. Oct. 2012;4(5):446-7. doi: 10.3978/j.issn.2072-1439.2012.08.15.

Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.

Picot, J. et al. "A biomimetic microfluidic chip to study the circulation and mechanical retention of red blood cells in the spleen" Am J Hematology (Jan. 12, 2015) 90(4):339-345.

Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.

Richardson, et al. Novel inhibition of archaeal family-D DNA polymerase by uracil. Nucleic acids research 41.7 (2013): 4207-4218.

Rogozin, et al. A highly conserved family of inactivated archaeal B family DNA polymerases. Biol Direct. Aug. 6, 2008 ;3:32. doi: 10.1186/1745-6150-3-32.

Schmeider, et al. Fast identification and removal of sequence contamination from genomic and metagenomic datasets. PLoS One. Mar. 9, 2011;6(3):e17288. doi:.10.1371/journal.pone.0017288.

Shuttleworth, et al. Recognition of the pro-mutagenic base uracil by family B DNA polymerases from archaea. J Mol Biol. Mar. 26, 2004;337(3):621-34.

Tayyab, S. et al. "Size exclusion chromatography and size exclusion HPLC of proteins" Biochem Ed, Pergamon, (1991) 19(3):149-152.

Zheng, X.Y. et al. "Haplotyping germline and cancer genomes with high-throughput linked-read sequencing" Nature Biotech (Feb. 1, 2016) 34(3):303-311.

Office action dated Sep. 25, 2015 for U.S. Appl. No. 14/250,701.

International search report and written opinion dated Aug. 20, 2014 for PCT/US2014/015424.

* cited by examiner

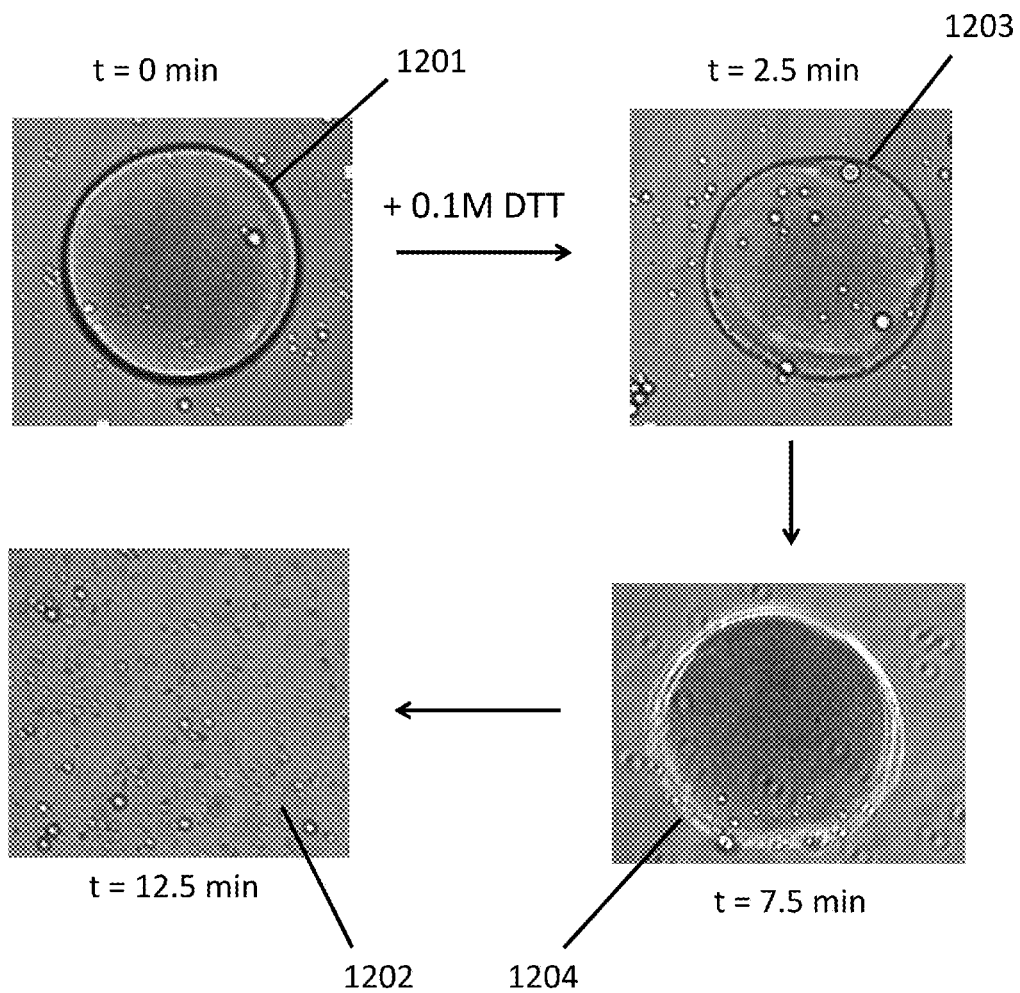

PARTITIONING AND PROCESSING OF ANALYTES AND OTHER SPECIES

CROSS-REFERENCE

This application claims the benefit of U.S. Provisional Patent Application No. 61/762,435, filed Feb. 8, 2013, U.S. Provisional Patent Application No. 61/800,223, filed Mar. 15, 2013, U.S. Provisional Patent Application No. 61/840,403, filed Jun. 27, 2013, and U.S. Provisional Patent Application No. 61/844,804, filed Jul. 10, 2013, said applications are incorporated herein by reference in their entireties for all purposes.

BACKGROUND

The partitioning and processing of species such as analytes and reagents is important for a variety of applications, including molecular biology applications and medical applications. Appropriate sample preparation is often needed prior to performing a reaction such as a polynucleotide sequencing reaction or an analyte detection reaction. For example, a sample such as a biological sample, including a collection of cells, tissue, and/or nucleic acids may need to be lysed, fragmented, or otherwise manipulated in order to permit downstream analysis. Sample preparation may also involve isolating certain molecules, and/or attaching unique identifiers to certain molecules, among other processes. There is a need in the art for improved methods, compositions, systems, devices, and kits for partitioning and processing of species.

SUMMARY

This disclosure provides methods, compositions, systems, devices, and kits for partitioning and processing of species. The exemplary embodiments provided in this summary are, in no way, intended to be limiting, and are only provided for illustrative purposes. Other embodiments are disclosed throughout this disclosure.

I. Capsules within Droplets

In some cases, the disclosure provides compositions comprising a plurality of capsules, the capsules situated within droplets in an emulsion, wherein the capsules are configured to release their contents into the droplets upon the application of a stimulus.

In some cases, the capsules comprise a species selected from the group consisting of a reagent and an analyte. In some cases, the droplets comprise a species selected from the group consisting of a reagent and an analyte.

In some cases a reagent is a protein, a polynucleotide, an enzyme, an antibody, a barcode, an adapter, a buffer, a small molecule, a detergent, a dye, a polymer and combinations thereof. In some cases, a reagent is an enzyme selected from the group consisting of a proteinase, a restriction enzyme, a ligase, a polymerase, a fragmentase, a reverse transcriptase, a transposase, and combinations thereof. In some cases an enzyme is a restriction enzyme that is a rare cutter. A reagent that is a barcode may be, for example, an oligonucleotide barcode.

An analyte may be any suitable analyte, for example a cell, a polynucleotide, a chromosome, a protein, a peptide, a polysaccharide, a sugar, a lipid, a small molecule, and combinations thereof. In some cases, an analyte is a polynucleotide. In some cases, the polynucleotide is selected from the group consisting of DNA, RNA, cDNA, and combinations thereof. In some cases, the amount of polynucleotide in a composition disclosed herein is about 1-3 ng. In some cases, the amount of polynucleotide in a composition disclosed herein is an amount sufficient to provide about 100-200X sequence coverage.

In some cases, a capsule may comprise on average, about one chromosome per capsule.

In some cases, each droplet may comprise, on average, about 1 capsule per droplet. In some cases, each droplet can hold, at most, a single capsule.

In some cases, at least one of the capsules comprises a further partition. The further partition may be, for example, selected from the group consisting of a capsule and a droplet in an emulsion.

In some cases, at least one of the capsules has a shell selected from the group consisting of a polymeric shell, a hydrogel, a hydrophilic shell, a hydrophobic shell, a shell with a net positive charge, a shell with a net negative charge, a shell with a neutral charge, and combinations thereof. In some cases, a capsule is formed from a hydrogel droplet.

In some cases, a capsule is responsive to a stimulus is selected from the group consisting of a chemical stimulus, a bulk stimulus, a biological stimulus, a light stimulus, a thermal stimulus, a magnetic stimulus, and combinations thereof. In some cases, a thermal stimulus comprises causing the composition to reach a temperature of at least 32 degrees Celsius. In some cases, the stimulus is selected from the group consisting of a change in pH, a change in ion concentration, reduction of disulfide bonds, and combinations thereof.

In some cases, capsules have a mean diameter of 1 micron to 250 microns, 1 micron to 100 microns, 1 micron to 50 microns, 10 microns to 100 microns, or 50 microns to 100 microns. In some cases droplets have a mean diameter of about 1 micron to about 250 microns, 1 micron to 100 microns, 1 micron to 50 microns, 10 microns to 100 microns, or 50 microns to 100 microns.

In some cases capsules have a mean volume of 1 picoliter to 1 microliter, 1 picoliter to 0.5 microliters, 1 picoliter to 0.1 microliters, 100 picoliters to 0.1 microliters, or 100 nanoliters to 500 nanoliters. In some cases droplets have a mean volume of about 1 picoliter to about 1 microliter, 1 picoliter to 0.5 microliters, 1 picoliter to 0.1 microliters, 100 picoliters to 0.1 microliters, or 100 nanoliters to 500 nanoliters.

In some cases the droplets comprise a fluid that is of a lesser density than the density of the capsules. In some cases the droplets comprise a fluid that is of a greater density than the density of the capsules.

In some cases capsules are produced by a method selected from the group consisting of emulsification polymerization, layer-by-layer assembly with polyelectrolytes, coacervation, internal phase separation, flow focusing, and combinations thereof.

In some cases a stimulus is applied to the capsules. In some cases a stimulus is applied to the droplets.

II. Capsules in Capsules

In some cases this disclosure provides compositions comprising a plurality of outer capsules, the outer capsules comprising at least one inner capsule, wherein the at least one inner capsule is configured to release its contents into at least one outer capsule among the plurality of outer capsules upon the application of a stimulus.

In some cases the inner capsule comprises a species selected from the group consisting of a reagent and an analyte. In some cases the outer capsules comprise a species selected from the group consisting of a reagent and an analyte.

In some cases the reagent is selected from the group consisting of a protein, a polynucleotide, an enzyme, an antibody, a barcode, an adapter, a buffer, a small molecule, a detergent, a dye, a polymer and combinations thereof. In some cases an enzyme is selected from the group consisting of a proteinase, a restriction enzyme, a ligase, a polymerase, a fragmentase, a reverse transcriptase, a transposase, and combinations thereof. In some cases the restriction enzyme is a restriction enzyme that is a rare cutter. In some cases the reagent is a barcode that is an oligonucleotide barcode.

In some cases the analyte is selected from the group consisting of a cell, a polynucleotide, a chromosome, a protein, a peptide, a polysaccharide, a sugar, a lipid, a small molecule, and combinations thereof. In some cases the analyte is a polynucleotide. In some cases the polynucleotide is selected from the group consisting of DNA, RNA, cDNA, and combinations thereof. In some cases the amount of the polynucleotide in a composition of this disclosure is about 1-3 ng. In some cases the amount of the polynucleotide in a composition of this disclosure is an amount sufficient to provide about 100-200X sequence coverage.

In some cases capsule comprises, on average, about one chromosome. In some cases each outer capsule comprises, on average, about 1 inner capsule per outer capsule. In some cases each outer capsule can hold, at most, a single inner capsule.

In some cases at least one inner capsule comprises a further partition. In some cases, the further partition is selected from the group consisting of a capsule and a droplet in an emulsion.

In some cases a capsule has a shell selected from the group consisting of a polymeric shell, a hydrogel, a hydrophilic shell, a hydrophobic shell, a shell with a net positive charge, a shell with a net negative charge, a shell with a neutral charge, and combinations thereof.

In some cases a capsule is responsive to a stimulus is selected from the group consisting of a chemical stimulus, a bulk stimulus, a biological stimulus, a light stimulus, a thermal stimulus, a magnetic stimulus, and combinations thereof. In some cases the thermal stimulus comprises causing the composition to reach a temperature of at least 32 degrees Celsius. In some cases the stimulus is selected from the group consisting of a change in pH, a change in ion concentration, reduction of disulfide bonds, and combinations thereof.

In some cases the inner capsules have a mean diameter of 1 micron to 250 microns, 1 micron to 100 microns, 1 micron to 50 microns, 10 microns to 100 microns, or 50 microns to 100 microns. In some cases the outer capsules have a mean diameter of 1 micron to 250 microns, 1 micron to 100 microns, 1 micron to 50 microns, 10 microns to 100 microns, or 50 microns to 100 microns.

In some cases the inner capsules have a mean volume of 1 picoliter to 1 microliter, 1 picoliter to 0.5 microliters, 1 picoliter to 0.1 microliters, 100 picoliters to 0.1 microliters, or 100 nanoliters to 500 nanoliters. In some cases the outer capsules have a mean volume of 1 picoliter to 1 microliter, 1 picoliter to 0.5 microliters, 1 picoliter to 0.1 microliters, 100 picoliters to 0.1 microliters, or 100 nanoliters to 500 nanoliters.

In some cases the outer capsules comprise a fluid that is of a lesser density than the density of the inner capsules. In some cases the outer capsules comprise a fluid that is of a greater density than the density of the inner capsules.

In some cases the capsules are produced by a method selected from the group consisting of emulsification polymerization, layer-by-layer assembly with polyelectrolytes, coacervation, internal phase separation, flow focusing, and combinations thereof.

In some cases the stimulus is applied to the inner capsule. In some cases the stimulus is applied to the outer capsule.

III. Spots in Wells

In some cases this disclosure provides a composition comprising a plurality of discrete spots disposed on a surface within a well, wherein each spot comprises a species and the spots are configured to release the species upon application of a stimulus. In some cases the species is selected from the group consisting of a reagent and an analyte. In some cases a composition of this disclosure further comprises a medium, wherein the medium comprises a species selected from the group consisting of a reagent and an analyte.

In some cases the reagent is selected from the group consisting of a protein, a polynucleotide, an enzyme, an antibody, a barcode, an adapter, a buffer, a small molecule, a detergent, a dye, a polymer and combinations thereof. In some cases the enzyme is selected from the group consisting of a proteinase, a restriction enzyme, a ligase, a polymerase, a fragmentase, a reverse transcriptase, a transposase, and combinations thereof. In some cases the restriction enzyme is a restriction enzyme that is a rare cutter. In some cases the barcode is an oligonucleotide barcode.

In some cases the analyte is selected from the group consisting of a cell, a polynucleotide, a chromosome, a protein, a peptide, a polysaccharide, a sugar, a lipid, a small molecule, and combinations thereof. In some cases the analyte is a polynucleotide. In some cases polynucleotide is selected from the group consisting of DNA, RNA, cDNA, and combinations thereof. In some cases the amount of the polynucleotide in the composition is about 1-3 ng. In some cases the amount of the polynucleotide in a composition of this disclosure is an amount sufficient to provide about 100-200X sequence coverage.

In some cases each well comprises at least 4 spots. In some cases at least one of the spots comprises a further partition. In some cases the further partition is selected from the group consisting of a capsule and a droplet in an emulsion.

In some cases the stimulus that releases a species from a spot is the introduction of a medium comprising an analyte into the well.

In some cases the spots have a mean diameter of about 1 micron to about 250 microns, 1 micron to 150 microns, 1 micron to 100 microns, 1 micron to 50 microns, 1 micron to 25 microns, or 1 micron to 10 microns.

IV. Devices Comprising Capsules in Droplets

In some cases this disclosure provides devices comprising a plurality of partitions, wherein at least one partition of the plurality of partitions comprises a capsule, wherein the capsule is situated within a droplet in an emulsion, wherein the capsule is configured to release its contents into the droplet upon the application of a stimulus. In some cases the plurality of partitions are selected from the group consisting of wells and spots.

In some cases the device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases the device comprises at least 1,000 partitions. In some cases the partitions have a density selected from the group consisting of at least about 1,000 partitions/$cm^2$ and at least about 10,000 partitions/$cm^2$.

In some cases the partitions are disposed along a fluid flow path having a fluid inlet and a fluid outlet.

In some cases the partitions are wells are disposed within a glass slide. In some cases the partitions are spots disposed on a glass slide.

In some cases the partitions have an interior surface comprising a hydrophilic material. In some cases a surface exterior to the partitions comprises a hydrophobic material. In some cases a fluid flow path comprises a surface comprising a hydrophobic material.

IV. Devices Comprising Capsules in Capsules

In some cases this disclosure provides devices comprising a plurality of partitions, wherein at least one partition of the plurality of partitions comprises an outer capsule, the outer capsule comprising at least one inner capsule, wherein the at least one inner capsule is configured to release its contents into the outer capsule upon the application of a stimulus. In some cases the plurality of partitions are selected from the group consisting of wells and spots.

In some cases the device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases the device comprises at least 1,000 partitions. In some cases the partitions have a density selected from the group consisting of at least about 1,000 partitions/$cm^2$ and at least about 10,000 partitions/$cm^2$.

In some cases the partitions are disposed along a fluid flow path having a fluid inlet and a fluid outlet.

In some cases the partitions are wells are disposed within a glass slide. In some cases the partitions are spots disposed on a glass slide.

In some cases the partitions have an interior surface comprising a hydrophilic material. In some cases a surface exterior to the partitions comprises a hydrophobic material. In some cases the fluid flow path comprises a surface comprising a hydrophobic material.

IV. Devices Comprising Spots in Wells

In some cases this disclosure provides devices comprising a plurality of wells, wherein at least one well of the plurality of wells comprises a plurality of discrete spots disposed on a surface within the well, wherein each spot comprises a species and the spots are configured to release the species upon application of a stimulus.

In some cases the device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases the device comprises at least 1,000 wells. In some cases the wells have a density selected from the group consisting of at least about 1,000 wells/$cm^2$ and at least about 10,000 wells/$cm^2$.

In some cases the wells are disposed along a fluid flow path having a fluid inlet and a fluid outlet.

In some cases the wells are disposed within a glass slide. In some cases the spots are disposed on a glass slide.

In some cases the wells have an interior surface comprising a hydrophilic material. In some cases a surface exterior to the wells comprises a hydrophobic material. In some cases the fluid flow path comprises a surface comprising a hydrophobic material.

IV. Methods Utilizing Capsules in Droplets

In some cases this disclosure provides a method comprising: (a) providing a plurality of capsules, the capsules situated within droplets in an emulsion, wherein the capsules are configured to release their contents into the droplets upon the application of a stimulus; and (b) providing a stimulus to cause the capsules to release their contents into the droplets.

In some cases the capsules comprise a species selected from the group consisting of a reagent and an analyte. In some cases the droplets comprise a species selected from the group consisting of a reagent and an analyte.

In some cases causing the capsules to release their contents into the droplets results in contact between a polynucleotide and an enzyme. In some cases causing the capsules to release their contents into the droplets results in contact between a polynucleotide and a barcode.

In some cases the analyte is a polynucleotide present in a predetermined coverage amount.

In some cases the method further comprises the step of sequencing the polynucleotide. In some cases the method further comprises the step of performing a polynucleotide phasing analysis.

V. Methods Utilizing Capsules in Capsules

In some cases this disclosure provides a method comprising: (a) providing a plurality of inner capsules, the inner capsules situated within outer capsules, wherein the inner capsules are configured to release their contents into the outer capsules upon the application of a stimulus; and (b) providing a stimulus to cause the inner capsules to release their contents into the outer capsules.

In some cases the inner capsules comprise a species selected from the group consisting of a reagent and an analyte. In some cases the outer capsules comprise a species selected from the group consisting of a reagent and an analyte.

In some cases causing the inner capsules to release their contents into the outer capsules results in contact between a polynucleotide and an enzyme. In some cases causing the inner capsules to release their contents into the outer capsules results in contact between a polynucleotide and a barcode.

In some cases the analyte is a polynucleotide present in a predetermined coverage amount.

In some cases the method further comprises the step of sequencing the polynucleotide. In some cases the method further comprises the step of performing a polynucleotide phasing analysis.

VI. Methods Utilizing Spots in Wells

In some cases this disclosure provides a method comprising: (a) providing a well comprising a plurality of discrete spots disposed on a surface within the well, wherein each spot comprises a species and the spots are configured to release the species upon application of a stimulus; (b) adding a medium comprising a species to the well; and (c) providing a stimulus to cause the spots to release their contents into the well.

In some cases the spots comprise a species selected from the group consisting of a reagent and an analyte. In some cases the medium comprises a species selected from the group consisting of a reagent and an analyte.

In some cases causing the spots to release their contents into the well results in contact between a polynucleotide and an enzyme. In some cases causing the spots to release their contents into the well results in contact between a polynucleotide and a barcode.

In some cases the analyte is a polynucleotide present in a predetermined coverage amount.

In some cases the method further comprises the step of sequencing the polynucleotide. In some cases the method further comprises the step of performing a polynucleotide phasing analysis.

VI. Methods of Encapsulating Polynucleotides, Including Whole Chromosomes

In some cases this disclosure provides a method comprising: (a) providing a sample comprising a cell; (b) lysing the cell, thereby generating a lysate; and (c) partitioning the lysate into a capsule.

In some cases the sample comprises a plurality of cells. In some cases the plurality of cells comprises 1 to 100,000 cells, 10 to 10,000 cells, 100 to 5,000 cells, or 1,000 to 5,000 cells.

In some cases lysing comprises a treatment with a proteinase. In some cases the proteinase is proteinase K.

In some cases after the partitioning, at least one of the capsules comprises a single copy of a polynucleotide from the cell. In some cases, at least one capsule comprises a mixture of polynucleotides, wherein none of the polynucleotides in the mixture are overlapping.

In some cases the polynucleotide is a chromosome.

In some cases the capsule comprises a shell with pores that restrict trans-shell transport of the polynucleotide but allow trans-shell transport of a species. In some cases the method further comprises the step of transporting an inner species from the interior of the capsule to the exterior of the capsule. In some cases the inner species is selected from the group consisting of a component of a buffer, a component of a cell, and a macromolecule. In some cases the method further comprises the step of transporting an outer species from the exterior of the capsule to the interior of the capsule. In some cases the outer species is selected from the group consisting of a reagent, a protein, a polynucleotide, an enzyme, an antibody, a barcode, an adapter, a buffer, a small molecule, a detergent, a dye, a polymer and combinations thereof. In some cases the outer species is a reagent for nucleic acid amplification.

In some cases the method further comprises the step of amplifying the encapsulated polynucleotide. In some cases the amplifying is performed by a method selected from the group consisting of multiple displacement amplification, polymerase chain reaction, ligase chain reaction, helicase-dependent amplification, and combinations thereof.

In some cases the method further comprises the step of fragmenting the encapsulated polynucleotide, thereby generating a fragmented polynucleotide. In some cases the method further comprises the step of attaching a barcode to the fragmented polynucleotide.

In some cases the method further comprises the step of placing the capsule comprising polynucleotide (or processed polynucleotide) into a partition. In some cases the partition is selected from the group consisting of a well, a droplet in an emulsion, and a capsule.

In some cases the capsule comprising the polynucleotide is configured to release its contents upon the application of a stimulus. In some cases the stimulus is selected from the group consisting of a chemical stimulus, a bulk stimulus, a biological stimulus, a light stimulus, a thermal stimulus, a magnetic stimulus, and combinations thereof.

In some cases the method further comprises the step of performing a polynucleotide phasing analysis.

VII. Kits

In some cases this disclosure provides kits. In some cases the disclosure provides kits for generating capsules within droplets in an emulsion, the kits comprising reagents for generating capsules, reagents for generating an emulsion, and instructions for generating the capsules within droplets in an emulsion. In some cases the capsules are configured to release their contents into the droplets upon the application of a stimulus. In some cases the kits further comprise a species for inclusion in a partition selected from the group consisting of the capsules, the droplets, and combinations thereof.

In some cases, this disclosure provides kits for generating capsules within capsules, the kits comprising reagents for generating inner capsules, reagents for generating outer capsules, and instructions for generating capsules within capsules. In some cases the inner capsules are configured to release their contents into the outer capsules upon the application of a stimulus. In some cases, the kits further comprise a species for inclusion in a partition selected from the group consisting of the inner capsules, the outer capsules, and combinations thereof.

In some cases this disclosure provides kits comprising a plurality of discrete spots disposed on a surface within a well, wherein each spot comprises a species and the spots are configured to release the species upon application of a stimulus, and instructions for use of the kit to process a sample. In some cases the stimulus is the addition of a sample to the well.

VIII. Partitioning and Fragmenting Methods

In some cases this disclosure provides a method of partitioning polynucleotides comprising: (a) isolating polynucleotides from a source of polynucleotides; (b) partitioning the polynucleotides at a predetermined coverage amount, to produce a plurality of partitions, wherein at least one partition comprises a mixture of non-overlapping polynucleotides, thereby generating partitioned polynucleotides; and (c) fragmenting the partitioned polynucleotides, thereby generating fragmented polynucleotides.

In some cases the source is a cell.

In some cases at least about 50% of the partitions comprise a mixture of non-overlapping polynucleotides.

In some cases the method further comprises the step of amplifying the partitioned polynucleotides. In some cases, the method further comprises the step of barcoding the fragmented polynucleotides.

In some cases this disclosure provides a method of fragmenting a polynucleotide comprising: (a) providing a polynucleotide; (b) encapsulating the polynucleotide, thereby generating an encapsulated polynucleotide; and (c) fragmenting the polynucleotide, thereby generating an encapsulated fragmented polynucleotide.

In some cases the fragmenting is performed by ultrasonic waves.

In some cases the encapsulating disposes the polynucleotide within a capsule. In some cases the encapsulating disposes the polynucleotide within a droplet of a hydrogel.

In some cases the method further comprises the step of encapsulating the encapsulated polynucleotide within a capsule. In some cases the method further comprises the step of encapsulating the encapsulated polynucleotide within a droplet of a hydrogel.

An additional aspect of the disclosure provides the use of a composition, device, method, or kit described herein in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, in circulating tumor cell (CTC) sequencing, in polynucleotide phasing, in sequencing polynucleotides from small numbers of cells, in analyzing gene expression, in partitioning polynucleotides from cells, or in a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of methods, compositions, systems, and devices of this disclosure are set forth with particularity in the appended claims. A better understanding of the features and advantages of this disclosure will be obtained by reference to the following detailed description that sets forth illustrative embodiments, in which the principles of the methods, compositions, systems, and devices of this disclosure are utilized, and the accompanying drawings of which:

FIG. 12 provides micrographs of chemically-responsive capsules formed as described in Example 4.

DETAILED DESCRIPTION

Figure 1A:
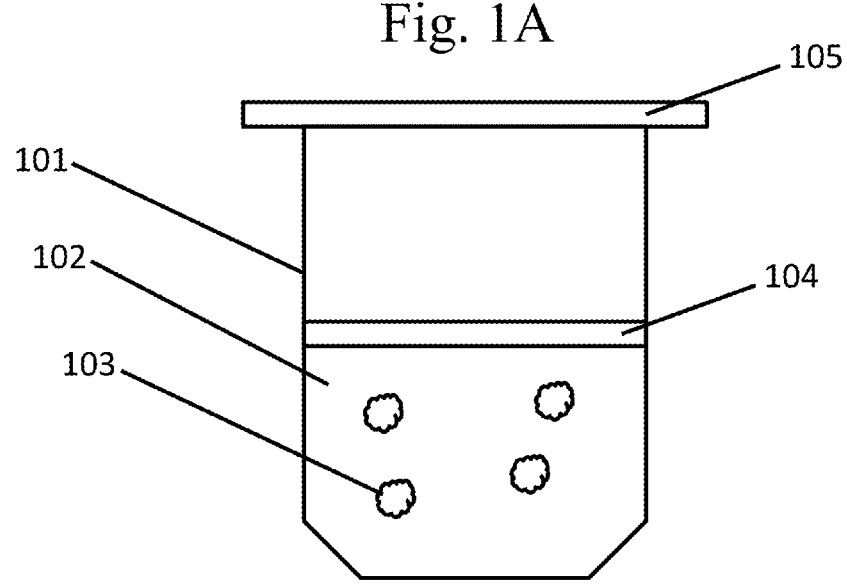
FIGS. 1A-B are schematic examples of wells comprising other types of partitions.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

This disclosure provides methods, compositions, systems, devices, and kits for partitioning and processing of species. A species may be contained within a sample that may also comprise other species. The sample may be partitioned. A sample may comprise any suitable species, as described more fully elsewhere in this disclosure. In some cases, a sample comprises a species that is a reagent or an analyte. The methods, compositions, systems, devices, and kits may be used for a variety of applications. Analyte may be processed for any suitable application, including, for example, processing polynucleotides for polynucleotide sequencing. Polynucleotides sequencing includes the sequencing of whole genomes, detection of specific sequences such as single nucleotide polymorphisms (SNPs) and other mutations, detection of nucleic acid (e.g., deoxyribonucleic acid) insertions, and detection of nucleic acid deletions.

Utilization of the methods, compositions, systems, devices, and kits described herein may incorporate, unless otherwise indicated, any conventional techniques of organic chemistry, polymer technology, microfluidics, molecular biology, recombinant techniques, cell biology, biochemistry, and immunology. Such conventional techniques include well and microwell construction, capsule generation, generation of emulsions, spotting, microfluidic device construction, polymer chemistry, restriction digestion, ligation, cloning, polynucleotide sequencing, and polynucleotide sequence assembly. Specific, non-limiting, illustrations of suitable techniques are described throughout this disclosure. However, equivalent procedures may also be utilized. Descriptions of certain techniques may be found in standard laboratory manuals, such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), and "Oligonucleotide Synthesis: A Practical Approach" 1984, IRL Press London, all of which are herein incorporated in their entirety by reference for all purposes.

I. DEFINITIONS

The terminology used herein is for the purpose of describing particular embodiments only and is not intended to be limiting.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising".

The term "about," as used herein, generally refers to a range that is 15% greater than or less than a stated numerical value within the context of the particular usage. For example, "about 10" would include a range from 8.5 to 11.5.

The term "barcode," as used herein, generally refers to a label that may be attached to an analyte to convey information about the analyte. For example, a barcode may be a polynucleotide sequence attached to all fragments of a target polynucleotide contained within a particular partition. This barcode may then be sequenced with the fragments of the target polynucleotide. The presence of the same barcode on multiple sequences may provide information about the origin of the sequence. For example, a barcode may indicate that the sequence came from a particular partition and/or a proximal region of a genome. This may be particularly useful when several partitions are pooled before sequencing.

The term "bp," as used herein, generally refers to an abbreviation for "base pairs".

The term "microwell," as used herein, generally refers to a well with a volume of less than 1 mL. Microwells may be made in various volumes, depending on the application. For example, microwells may be made in a size appropriate to accommodate any of the partition volumes described herein.

The term "partition," as used herein, may be a verb or a noun. When used as a verb (e.g., "to partition," or "partitioning"), the term generally refers to the fractionation (subdivision) of a species or sample (e.g., a polynucleotide) between vessels that can be used to sequester one fraction (or subdivision) from another. Such vessels are referred to using the noun "partition." Partitioning may be performed, for example, using microfluidics, dilution, dispensing, and the like. A partition may be, for example, a well, a microwell, a hole, a droplet (e.g., a droplet in an emulsion), a continuous phase of an emulsion, a test tube, a spot, a capsule, or any other suitable container for sequestering one fraction of a sample from another.

The terms "polynucleotide" or "nucleic acid," as used herein, generally refer to molecules comprising a plurality of nucleotides. Exemplary polynucleotides include deoxyribonucleic acids, ribonucleic acids, and synthetic analogues thereof, including peptide nucleic acids.

The term "species," as used herein, generally refers to any substance that can be used with the methods, compositions, systems, devices, and kits of this disclosure. Examples of species include reagents, analytes, cells, chromosomes, tagging molecules or groups of molecules, barcodes, and any sample comprising any of these species. Any suitable species may be used, as more fully discussed elsewhere in this disclosure.

II. PARTITIONS a. General Characteristics of Partitions

As described throughout this disclosure, certain methods, compositions, systems, devices, and kits of the disclosure may utilize the subdivision (partitioning) of certain species into separate partitions. A partition may be, for example, a well, a microwell, a hole, a droplet (e.g., a droplet in an emulsion), a continuous phase of an emulsion, a test tube, a spot, a bead (e.g., a gel bead, a paraffin bead, a wax bead), a capsule, or any other suitable container for sequestering one fraction of a sample or a species. In some cases, a capsule is a bead (e.g., a gel bead). Partitions may be used to contain a species for further processing. For example, if a species is a polynucleotide analyte, further processing may comprise cutting, ligating, and/or barcoding with species that are reagents. Any number of devices, systems or containers may be used to hold, support or contain partitions. In some cases, a microwell plate may be used to hold, support, or contain partitions. Any suitable microwell plate may be used, for example microwell plates having 96, 384, or 1536 wells.

Each partition may also contain, or be contained within any other suitable partition. For example, a well, microwell, hole, or tube may comprise a droplet (e.g., a droplet in an emulsion), a continuous phase in an emulsion, a spot, a capsule, or any other suitable partition. A droplet may comprise a capsule or another droplet. A capsule may comprise a droplet or another capsule. These descriptions are merely illustrative, and all suitable combinations and pluralities are also envisioned. For example, any suitable partition may comprise a plurality of the same or different partitions. In one example, a well or microwell comprises a plurality of droplets and a plurality of capsules. In another example, a capsule comprises a plurality of capsules and a plurality of droplets. All combinations of partitions are envisioned. Table 1 shows non-limiting examples of partitions that may be combined with each other.

TABLE 1

Examples of partitions that may be combined with each other.

| | Well | Spot | Droplet | Capsule |
|---|---|---|---|---|
| Well | Well inside well | Spot inside well | Droplet inside well | Capsule inside well |
| Spot | Spot inside well | Spot inside spot | Droplet inside spot | Capsule inside spot |
| Droplet | Droplet inside well | Droplet inside spot | Droplet inside droplet | Droplet inside capsule Capsule inside droplet |
| Capsule | Capsule inside well | Capsule inside spot Spot inside capsule | Capsule inside droplet Droplet inside capsule | Capsule inside capsule |

Any partition described herein may comprise multiple partitions. For example, a partition may comprise 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. A partition may comprise at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, a partition may comprise less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, each partition may comprise 2-50, 2-20, 2-10, or 2-5 partitions.

A partition may comprise any suitable species or mixture of species. For example, in some cases a partition may comprise a reagent, an analyte, a sample, a cell, and combinations thereof. A partition comprising other partitions may comprise certain species in the same partitions and certain species in different partitions. Species may be distributed between any suitable partitions, depending on the needs of the particular process. For example, any of the partitions in Table 1 may contain at least one first species and any of the partitions in Table 1 may contain at least one second species. In some cases the first species may be a reagent and the second species may be an analyte.

In some cases, a species is a polynucleotide isolated from a cell. For example, in some cases polynucleotides (e.g., genomic DNA, RNA, etc.) is isolated from a cell utilizing any suitable method (e.g., a commercially available kit). The polynucleotide may be quantified. The quantified polynucleotide may then be partitioned into a plurality of partitions as described herein. The partitioning of the polynucleotide may be performed at a predetermined coverage amount, according to the quantification and the needs of the assay. In some cases, all or most partitions do not comprise polynucleotides that overlap, such that separate mixtures of non-overlapping fragments are formed across the plurality of partitions. The partitioned polynucleotides may then be treated according to any suitable method known in the art or described in this disclosure. For example, the partitioned polynucleotides may be fragmented, amplified, barcoded, and the like.

Species may be partitioned using a variety of methods. For example, species may be diluted and dispensed across a plurality of partitions. A terminal dilution of a medium comprising species may be performed such that the number of partitions exceeds the number of species. Dilution may also be used prior to forming an emulsion or capsules, or prior to spotting a species on a substrate. The ratio of the number of species to the number of partitions may be about 0.1, 0.5, 1, 2, 4, 8, 10, 20, 50, 100, or 1000. The ratio of the number of species to the number of partitions may be at least about 0.1, 0.5, 1, 2, 4, 8, 10, 20, 50, 100, or 1000. The ratio of the number of species to the number of partitions may be less than about 0.1, 0.5, 1, 2, 4, 8, 10, 20, 50, 100, or 1000. The ratio of the number of species to the number of partitions may range from about 0.1-10, 0.5-10, 1-10, 2-10, 10-100, 100-1000, or more.

Partitioning may also be performed using piezoelectric droplet generation (e.g., Bransky et al., *Lab on a Chip*, 2009, 9, 516-520) or surface acoustic waves (e.g., Demirci and Montesano, *Lab on a Chip*, 2007, 7, 1139-1145).

The number of partitions employed may vary depending on the application. For example, the number of partitions may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000 or more. The number of partitions may be at least about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000 or more. The number of partitions may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

The volume of the partitions may vary depending on the application. For example, the volume of any of the partitions described in this disclosure (e.g., wells, spots, droplets (e.g., in an emulsion), and capsules) may be about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be at least about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be less than about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. the volume of the partitions may be about 0.5 fL-5 pL, 10 pL-10 nL, 10 nL-10 µl, 10 µl-100 µl, or 100 µl to 1 mL.

There may be variability in the volume of fluid in different partitions. More specifically, the volume of different partitions may vary by at least (or at most) plus or minus 1%, 2%, 3%, 4%, 5%, 10%, 20%, 30%, 40%, 50%, 60%, 70%, 80%, 90%, 100%, 200%, 300%, 400%, 500%, or 1000% across a set of partitions. For example, a well (or other partition) may comprise a volume of fluid that is at most 80% of the fluid volume within a second well (or other partition).

Particular species may also be targeted to specific partitions. For example, in some cases, a capture reagent (e.g., an oligonucleotide probe) may be immobilized or placed within a partition to capture specific species (e.g., polynucleotides).

The number of different species or different sets of species that are partitioned may vary depending upon, for example, the particular species to be partitioned and/or the application. Different sets of species may be, for example, sets of identical species where the identical species differ between each set. Or different sets of species may be, for example, sets of different species, where each set differs in its included species. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different species or different sets of species may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different species or different sets of species may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different species or different sets of species may be partitioned. In some examples, about 1-5, 5-10, 10-50, 50-100, 100-1000, 1000-10000, 10000-100000, 100000-1000000, 10000-1000000, 10000-10000000, or 10000-100000000 species may be partitioned.

Species may also be partitioned at a particular density. For example, species may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 species per partition. Species may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 or more species per partition. Species may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 species per partition. Species may be partitioned such that each partition contains about 1-5, 5-10, 10-50, 50-100, 100-1000, 1000-10000, 10000-100000, 100000-1000000, 10000-1000000, or 10000-10000000 species per partition.

Species may also be partitioned such that identical species are partitioned at a particular density. For example, identical species may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 identical species per partition. Species may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 or more identical species per partition. Species may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 identical species per partition. Species may be partitioned such that each partition contains about 1-5, 5-10, 10-50, 50-100, 100-1000, 1000-10000, 10000-100000, 100000-1000000, 10000-1000000, or 10000-10000000 identical species per partition.

Species may also be partitioned such that different species are partitioned at a particular density. For example, different species may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 different species per partition. Species may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 or more different species per partition. Species may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 different species per partition. Species may be partitioned such that each partition contains about 1-5, 5-10, 10-50, 50-100, 100-1000, 1000-10000, 10000-100000, 100000-1000000, 10000-1000000, or 10000-10000000 different species per partition.

As will be appreciated, any of the above-described different numbers of species may be provided with any of the above-described barcode densities per partition, and in any of the above-described numbers of partitions.

Species may be partitioned such that at least one partition comprises a species that is unique within that partition. This may be true for about 1%, 5%, 10%, 20%, 30%, 40%, 50%, 60%, 70%, 80%, 90%, or more of the partitions. This may be true for at least about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, or 90% of the partitions.

a. Wells as Partitions

In some cases, wells are used as partitions. The wells may be microwells. With reference to FIG. 1A, a well 101 may comprise a medium 102 comprising a species or plurality of species 103. Species may be contained within a well in various configurations. In one example, a species is dispensed directly into a well (e.g., FIG. 1A). A species dispensed directly into a well may be overlaid with a layer that is, for example, dissolvable, meltable, or permeable 104. This layer may be, for example, an oil, wax, membrane, or the like. The layer may be dissolved or melted prior to or after introduction of another species into the well. The well may be sealed at any point, with a sealing layer 105, for example after addition of any species.

In one example, reagents for sample processing are dispensed directly into a well and overlaid with a layer that is dissolvable, meltable, or permeable. A sample comprising an analyte to be processed is introduced on top of the layer. The layer is dissolved or melted, or the analyte (or reagent) diffuses through the layer. The well is sealed and incubated under appropriate conditions for the processing of the analyte. Processed analyte may then be recovered.

Figure 1B:
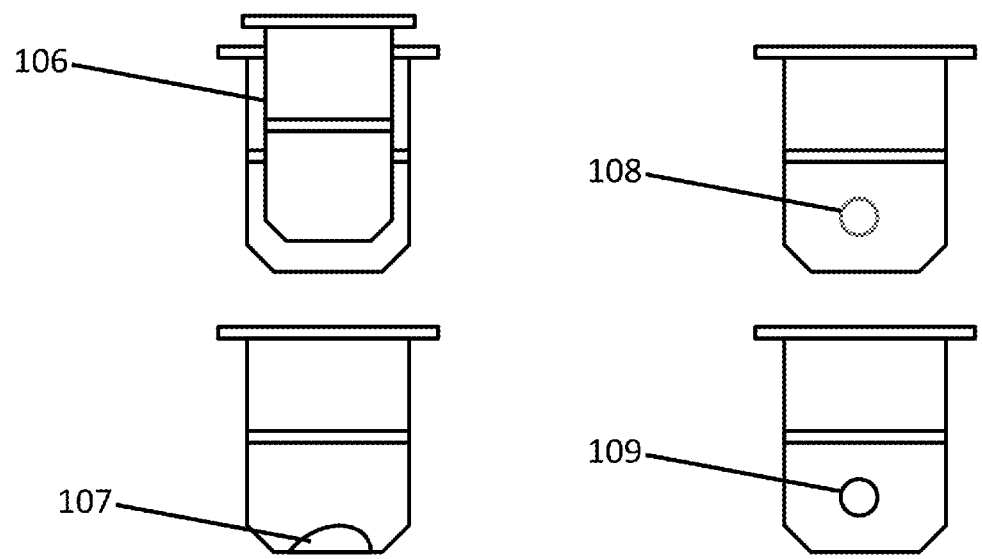

In some cases, wells comprise other partitions. A well may comprise any suitable partition including, for example, with reference to FIG. 1B, another well 106, a spot 107, a droplet (e.g., a droplet in an emulsion) 108, a capsule 109, and the like. Each partition may be present as a single partition or a plurality of partitions, and each partition may comprise the same species or different species.

In one example, a well comprises a capsule comprising reagents for sample processing. A capsule may be loaded into a well using a liquid medium, or loaded into a well without a liquid medium (e.g., essentially dry). As described elsewhere in this disclosure, a capsule may contain one or more capsules, or other partitions. A sample comprising an analyte to be processed is introduced into the well. The well is sealed and a stimulus is applied to cause release of the contents of the capsule into the well, resulting in contact between the reagents and the analyte to be processed. The well is incubated under appropriate conditions for the processing of the analyte. Processed analyte may then be recovered. While this example describes an embodiment where a reagent is in a capsule and an analyte is in the well, the opposite configuration—i.e., reagent in the well and analyte in the capsule—is also possible.

In another example, a well comprises an emulsion and the droplets of the emulsion comprise capsules comprising reagents for sample processing. A sample comprising an analyte to be processed is contained within the droplets of the emulsion. The well is sealed and a stimulus is applied to cause release of the contents of the capsules into the droplets, resulting in contact between the reagents and the analyte to be processed. The well is incubated under appropriate conditions for the processing of the analyte. Processed analyte may then be recovered. While this example describes an embodiment where a reagent is in a capsule and an analyte is in a droplet, the opposite configuration—i.e., reagent in the droplet and analyte in the capsule—is also possible.

Wells may be arranged as an array, for example a microwell array. Based on the dimensions of individual wells and the size of the substrate, the well array may comprise a range of well densities. In some cases, the well density may be 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In some cases, the well density may be at least 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In some cases, the well density may be less than 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$.

b. Spots as Partitions

Figure 2A:
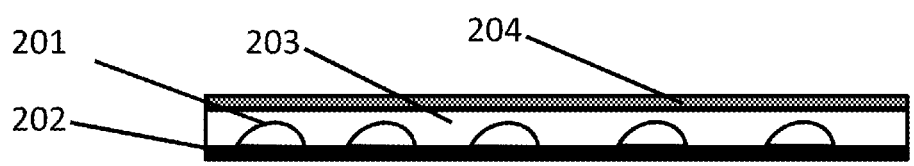
FIGS. 2A-B are schematic examples of spots comprising other types of partitions.

In some cases, spots are used as partitions. With reference to FIG. 2A, a spot may be made, for example, by dispensing a substance 201 on a surface 202. Species may be contained within a spot in various configurations. In one example, a species is dispensed directly into a spot by including the species in the medium used to form the spot. A species dispensed directly onto a spot may be overlaid with a layer that is, for example, dissolvable, meltable, or permeable 203. This layer may be, for example, an oil, wax, membrane, or the like. The layer may be dissolved or melted prior to or after introduction of another species onto the spot. The spot may be sealed at any point, for example after addition of any species, by an overlay 204.

In one example, reagents for sample processing are dispensed directly onto a spot, for example on a glass slide, and overlaid with a layer that is dissolvable, meltable, or permeable. A sample comprising an analyte to be processed is introduced on top of the layer. The layer is dissolved or melted, or the analyte (or reagent) diffuses through the layer. The spot is sealed and incubated under appropriate conditions for the processing of the analyte. Processed analyte may then be recovered.

As described elsewhere in this disclosure (e.g., Table 1), spots may also be arranged within a well. In some cases, a plurality of spots may be arranged within a well such that the contents of each spot do not mix. Such a configuration may be useful, for example, when it is desirable to prevent species from contacting each other. In some cases, a well may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, or more spots. In some cases, a well may comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or more spots. In some cases, a well may comprise less than 2, 3, 4, 5, 6, 7, 8, 9, 10, 11, 12, 13, 14, 15, 16, 17, 18, 19, 20, 21, 22, 23, 24, 25, 26, 27, 28, 29, or 30 spots. In some cases, a well may comprise 2-4, 2-6, 2-8, 4-6, 4-8, 5-10, or 4-12 spots. Upon addition of a substance (e.g., a medium containing an analyte) to the well, the species in the spot may mix. Moreover, using separate spots to contain different species (or combinations of species) may also be useful to prevent cross-contamination of devices used to place the spots inside the well.

Figure 2B:

In some cases, spots comprise other partitions. A spot may comprise any suitable partition including, for example, with reference to FIG. 2B, another spot 205, a droplet (e.g., a droplet in an emulsion) 206, a capsule 207, and the like. Each partition may be present as a single partition or a plurality of partitions, and each partition may comprise the same species or different species.

In one example, a spot comprises a capsule comprising reagents for sample processing. As described elsewhere in this disclosure, a capsule may contain one or more capsules, or other partitions. A sample comprising an analyte to be processed is introduced into the spot. The spot is sealed and a stimulus is applied to cause release of the contents of the capsule into the spot, resulting in contact between the reagents and the analyte to be processed. The spot is incubated under appropriate conditions for the processing of the analyte. Processed analyte may then be recovered. While this example describes an embodiment where a reagent is in a capsule and an analyte is in the spot, the opposite configuration—i.e., reagent in the spot and analyte in the capsule—is also possible.

In another example, a spot comprises an emulsion and the droplets of the emulsion comprise capsules comprising reagents for sample processing. A sample comprising an analyte to be processed is contained within the droplets of the emulsion. The spot is sealed and a stimulus is applied to cause release of the contents of the capsules into the droplets, resulting in contact between the reagents and the analyte to be processed. The spot is incubated under appropriate conditions for the processing of the analyte. Processed analyte may then be recovered. While this example describes an embodiment where a reagent is in a capsule and an analyte is in a droplet, the opposite configuration—i.e., reagent in the droplet and analyte in the capsule—is also possible.

Spots may be of uniform size or heterogeneous size. In some cases, the diameter of a spot may be about 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, 1 mm, 2 mm, 5 mm, or 1 cm. A spot may have a diameter of at least about 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, 1 mm, 1 mm, 2 mm, 5 mm, or 1 cm. In some cases, a spot may have a diameter of less than about 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, 1 mm, 1 mm, 2 mm, 5 mm, or 1 cm. In some cases, a spot may have a diameter of about 0.1 μm to 1 cm, 100 μm to 1 mm, 100 μm to 500 μm, 100 μm to 600 μm, 150 μm to 300 μm, or 150 μm to 400 μm.

Spots may be arranged as an array, for example a spot array. Based on the dimensions of individual spots and the size of the substrate, the spot array may comprise a range of spot densities. In some cases, the spot density may be 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$. In some cases, the spot density may be at least 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$. In some cases, the spot density may be less than 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$.

c. Emulsions as Partitions

In some cases, the droplets in an emulsion are used as partitions. An emulsion may be prepared, for example, by any suitable method, including methods known in the art. (See e.g., Weizmann et al., Nature Methods, 2006, 3(7):545-550; Weitz et al. U.S. Pub. No. 2012/0211084). In some cases, water-in-fluorocarbon emulsions may be used. These emulsions may incorporate fluorosurfactants such as oligomeric perfluorinated polyethers (PFPE) with polyethylene glycol (PEG). (Holtze et al., Lab on a Chip, 2008, 8(10): 1632-1639). In some cases, monodisperse emulsions may be formed in a microfluidic flow focusing device. (Garstecki et al., Applied Physics Letters, 2004, 85(13):2649-2651).

Figure 3A:
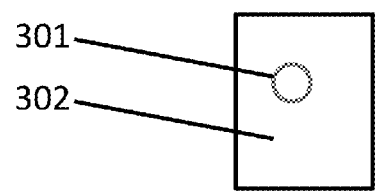
FIGS. 3A-B are schematic examples of a droplet of an emulsion comprising other types of partitions.

FIG. 3A illustrates exemplary embodiments. With reference to FIG. 3A, a species may be contained within a droplet 301 in an emulsion containing, for example, a first phase (e.g., oil or water) forming the droplet 301 and a second (continuous) phase (e.g., water or oil) 302. An emulsion may be a single emulsion, for example, a water-in-oil or an oil-in-water emulsion. An emulsion may be a double emulsion, for example a water-in-oil-in-water or an oil-in-water-in-oil emulsion. Higher-order emulsions are also possible. The emulsion may be held in any suitable container, including any suitable partition described in this disclosure.

Figure 3B:
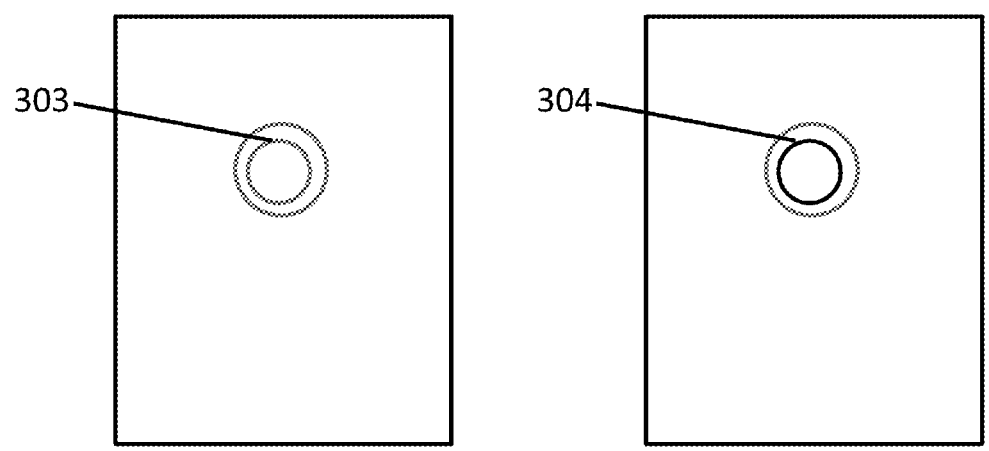

In some cases, droplets in an emulsion comprise other partitions. A droplet in an emulsion may comprise any suitable partition including, for example, with reference to FIG. 3B, another droplet (e.g., a droplet in an emulsion) 303, a capsule 304, and the like. Each partition may be present as a single partition or a plurality of partitions, and each partition may comprise the same species or different species.

In one example, a droplet in an emulsion comprises a capsule comprising reagents for sample processing. As described elsewhere in this disclosure, a capsule may contain one or more capsules, or other partitions. A sample comprising an analyte to be processed is contained within the droplet. A stimulus is applied to cause release of the contents of the capsule into the droplet, resulting in contact between the reagents and the analyte to be processed. The droplet is incubated under appropriate conditions for the processing of the analyte. Processed analyte may then be recovered. While this example describes an embodiment where a reagent is in a capsule and an analyte is in the droplet, the opposite configuration—i.e., reagent in the droplet and analyte in the capsule—is also possible.

The droplets in an emulsion may be of uniform size or heterogeneous size. In some cases, the diameter of a droplet in an emulsion may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. A droplet may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 150 µm to 200 µm, 150 µm to 300 µm, or 150 µm to 400 µm.

Droplets in an emulsion also may have a particular density. In some cases, the droplets are less dense than an aqueous fluid (e.g., water); in some cases, the droplets are denser than an aqueous fluid. In some cases, the droplets are less dense than a non-aqueous fluid (e.g., oil); in some cases, the droplets are denser than a non-aqueous fluid. Droplets may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Droplets may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, droplet densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

d. Capsules as Partitions

Figure 4A:
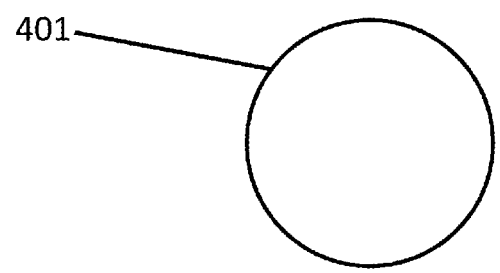
FIGS. 4A-B are schematic examples of capsules comprising other types of partitions.

In some cases, capsules are used as partitions. With reference to FIG. 4A, a capsule 401 may be prepared by any suitable method, including methods known in the art, including emulsification polymerization (Weitz et al. (U.S. Pub. No. 2012/0211084)), layer-by-layer assembly with polyelectrolytes, coacervation, internal phase separation, and flow focusing. Any suitable species may be contained within a capsule. The capsule may be held in any suitable container, including any suitable partition described in this disclosure.

Figure 4B:
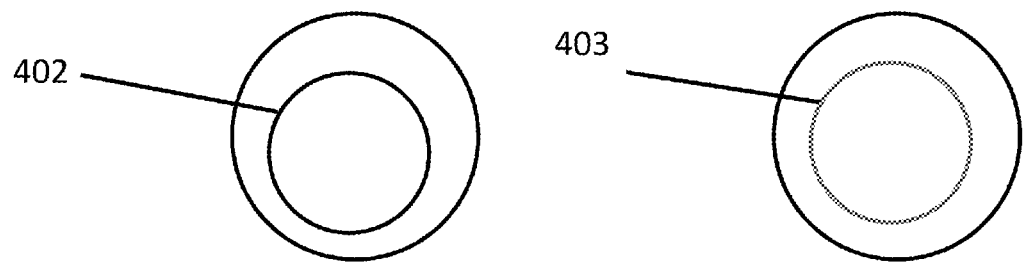

In some cases, capsules comprise other partitions. A capsule may comprise any suitable partition including, for example, with reference to FIG. 4B, another capsule 402, a droplet in an emulsion 403, and the like. Each partition may be present as a single partition or a plurality of partitions, and each partition may comprise the same species or different species.

In one example, an outer capsule comprises an inner capsule. The inner capsule comprises reagents for sample processing. An analyte is encapsulated in the medium between the inner capsule and the outer capsule. A stimulus is applied to cause release of the contents of the inner capsule into the outer capsule, resulting in contact between the reagents and the analyte to be processed. The outer capsule is incubated under appropriate conditions for the processing of the analyte. Processed analyte may then be recovered. While this example describes an embodiment where a reagent is in an inner capsule and an analyte in the medium between the inner capsule and the outer capsule, the opposite configuration—i.e., reagent in the medium between the inner capsule and the outer capsule, and analyte in the inner capsule—is also possible.

Capsules may be pre-formed and filled with reagents by injection. For example, the picoinjection methods described in Abate et al. (Proc. Natl. Acad. Sci. U.S.A., 2010, 107(45), 19163-19166) and Weitz et al. (U.S. Pub. No. 2012/0132288) may be used to introduce reagents into the interior of capsules described herein. Generally, the picoinjection will be performed prior to the hardening of the capsule shell, for example by injecting species into the interior of a capsule precursor, such as a droplet of an emulsion, before formation of the capsule shell.

Capsules may be of uniform size or heterogeneous size. In some cases, the diameter of a capsule may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. A capsule may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a capsule may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a capsule may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 150 µm to 200 µm, 150 µm to 300 µm, or 150 µm to 400 µm.

Capsules also may have a particular density. In some cases, the capsules are less dense than an aqueous fluid (e.g., water); in some cases, the capsules are denser than an aqueous fluid. In some cases, the capsules are less dense than a non-aqueous fluid (e.g., oil); in some cases, the capsules are denser than a non-aqueous fluid. Capsules may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Capsules may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, capsule densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

1. Production of Capsules by Flow Focusing

Figure 5:
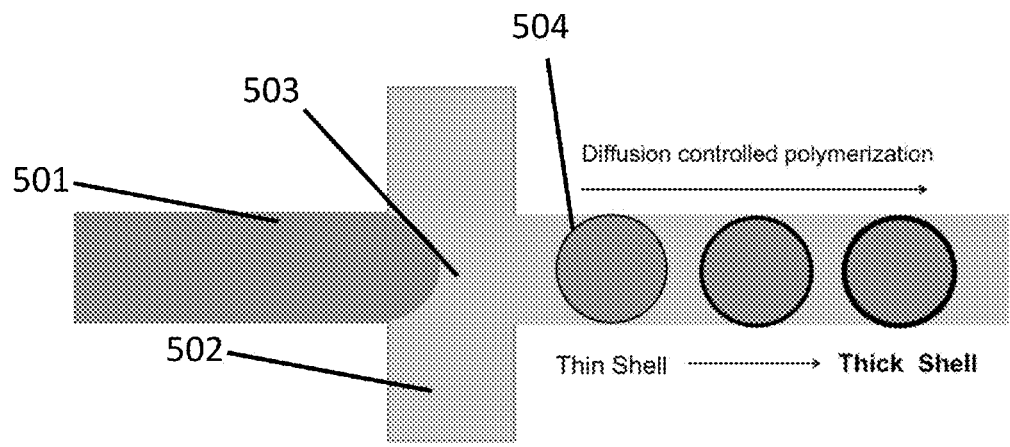
FIG. 5 is a schematic example of a flow focusing method for the production of capsules and/or emulsions.

In some cases, capsules may be produced by flow focusing. Flow focusing is a method whereby a first fluid that is immiscible with a second fluid is flowed into the second fluid. With reference to FIG. 5, a first (e.g., aqueous) fluid comprising a monomer, crosslinker, initiator, and aqueous surfactant 501 is flowed into a second (e.g., oil) fluid comprising a surfactant and an accelerator 502. After entering the second fluid at a T-junction in a microfluidic device 503, a droplet of first fluid breaks off from the first fluid stream and a capsule shell begins to form 504 due to the mixing of the monomer, crosslinker, and initiator in the first fluid and the accelerator in the second fluid. Thus, a capsule is formed. As the capsule proceeds downstream, the shell becomes thicker due to increased exposure to the accelerator. Varying the concentrations of the reagents may also be used to vary the thickness and permeability of the capsule shell.

A species, or other partition such as a droplet, may be encapsulated by, for example, including the species in the first fluid. Including the species in the second fluid may embed the species in the shell of the capsule. Of course, depending on the needs of the particular sample processing method, the phases may also be reversed—i.e., the first phase may be an oil phase and the second phase may be an aqueous phase.

2. Production of Capsules within Capsules by Flow Focusing

Figure 6:
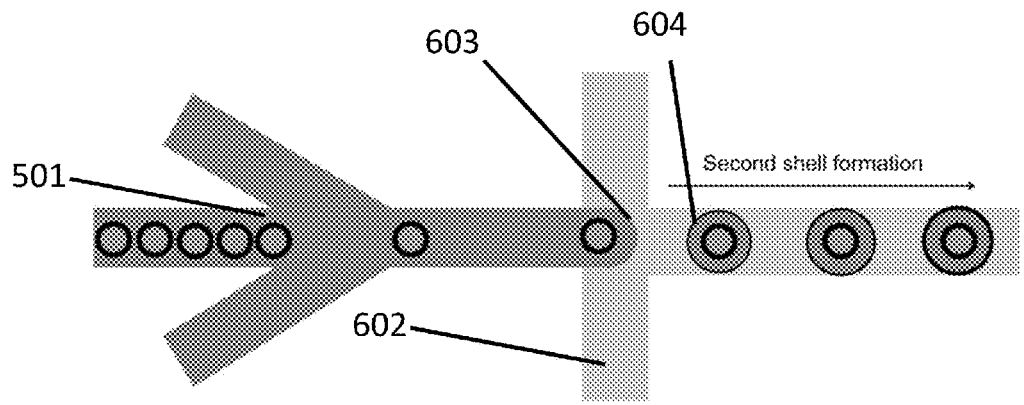
FIG. 6 is a schematic example of a flow focusing method for the production of capsules within capsules, capsules within droplets of an emulsion, or droplets of an emulsion within capsules.

In some cases, capsules within capsules may be produced by flow focusing. With reference to FIG. 6, a first (e.g., aqueous) fluid comprising a capsule, monomer, crosslinker, initiator, and aqueous surfactant 601 is flowed into a second (oil) fluid comprising a surfactant and an accelerator 602. After entering the second fluid at a T-junction in a microfluidic device 603, a droplet of first fluid breaks off from the first fluid stream and a second capsule shell begins to form around the capsule 604 due to the mixing of the monomer, crosslinker, and initiator in the first fluid and the accelerator in the second fluid. Thus, a capsule within a capsule is formed. As the capsule proceeds downstream, the shell becomes thicker due to increased exposure to the accelerator. Varying the concentrations of the reagents may also be used to vary the thickness and permeability of the second capsule shell.

A species may be encapsulated by, for example, including the species in the first fluid. Including the species in the second fluid may embed the species in the second shell of the capsule. Of course, depending on the needs of the particular sample processing method, the phases may also be reversed—i.e., the first phase may be an oil phase and the second phase may be an aqueous phase.

3. Production of Capsules in Batch

Figure 7:
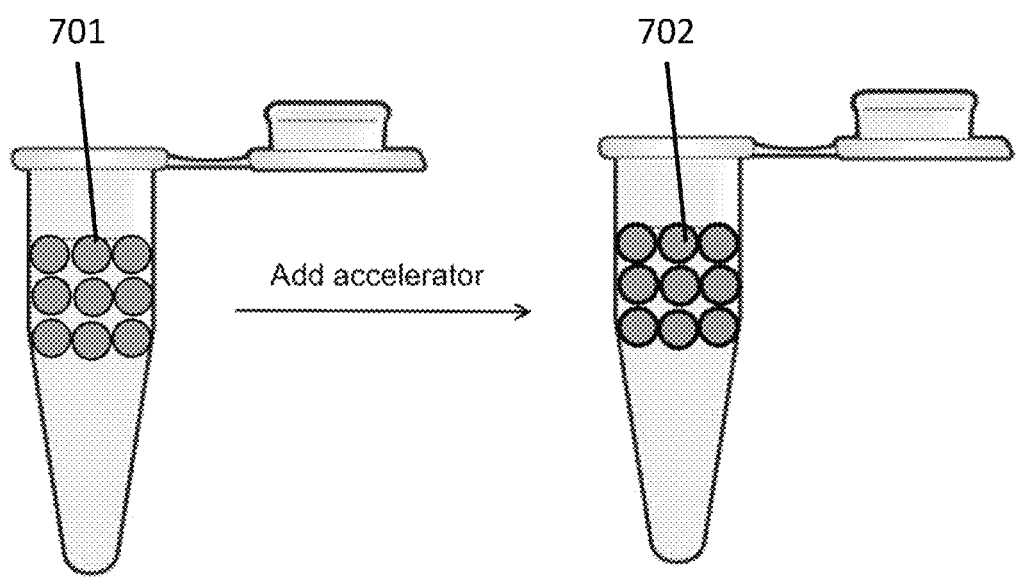
FIG. 7 is a schematic example of a method for the batch production of capsules.

In some cases, capsules may be produced in batch, using capsule precursors, such as the droplets in an emulsion. With reference to FIG. 7, capsule precursors 701 may be formed by any suitable method, for example by producing an emulsion with droplets comprising a monomer, a crosslinker, an initiator, and a surfactant. An accelerator may then be added to the medium, resulting in the formation of capsules 702. As for the methods of flow focusing, the thickness of the shell can be varied by varying the concentrations of the reactants, and the time of exposure to the accelerator. The capsules may then be washed and recovered. As for any method described herein, a species, including other partitions, may be encapsulated within the capsule or, if suitable, within the shell.

In another example, the droplets of an emulsion may be exposed to an accelerator that is present in an outlet well during the emulsion generation process. For example, capsule precursors may be formed by any suitable method, such as the flow focusing method illustrated in FIG. 5. Rather than including the accelerator in second fluid 502, the accelerator may be included in a medium located at the exit of the T-junction (e.g., a medium located at the far-right of the horizontal channel of FIG. 5. As the emulsion droplets (i.e., capsule precursors) exit the channel, they contact the medium comprising the accelerator (i.e., the outlet medium). If the capsule precursor has a density that is less than the density of outlet medium, the capsule precursors will rise through the medium, ensuring convectional and diffusional exposure to the accelerator and reducing the likelihood of polymerization at the outlet of the channel.

III. SPECIES

The methods, compositions, systems, devices, and kits of this disclosure may be used with any suitable species. A species can be, for example, any substance used in sample processing, such as a reagent or an analyte. Exemplary species include whole cells, chromosomes, polynucleotides, organic molecules, proteins, polypeptides, carbohydrates, saccharides, sugars, lipids, enzymes, restriction enzymes, ligases, polymerases, barcodes, adapters, small molecules, antibodies, fluorophores, deoxynucleotide triphosphates (dNTPs), dideoxynucleotide triphosphates (ddNTPs), buffers, acidic solutions, basic solutions, temperature-sensitive enzymes, pH-sensitive enzymes, light-sensitive enzymes, metals, metal ions, magnesium chloride, sodium chloride, manganese, aqueous buffer, mild buffer, ionic buffer, inhibitors, saccharides, oils, salts, ions, detergents, ionic detergents, non-ionic detergents, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, a locked nucleic acid (LNA) in whole or part, locked nucleic acid nucleotides, any other type of nucleic acid analogue, proteases, nucleases, protease inhibitors, nuclease inhibitors, chelating agents, reducing agents, oxidizing agents, probes, chromophores, dyes, organics, emulsifiers, surfactants, stabilizers, polymers, water, small molecules, pharmaceuticals, radioactive molecules, preservatives, antibiotics, aptamers, and the like. In summary, the species that are used will vary depending on the particular sample processing needs.

In some cases, a partition comprises a set of species that have a similar attribute (e.g., a set of enzymes, a set of minerals, a set of oligonucleotides, a mixture of different barcodes, a mixture of identical barcodes). In other cases, a partition comprises a heterogeneous mixture of species. In some cases, the heterogeneous mixture of species comprises all components necessary to perform a particular reaction. In some cases, such mixture comprises all components necessary to perform a reaction, except for 1, 2, 3, 4, 5, or more components necessary to perform the reaction. In some cases, such additional components are contained within a different partition or within a solution within or surrounding a partition.

A species may be naturally-occurring or synthetic. A species may be present in a sample obtained using any methods known in the art. In some cases, a sample may be processed before analyzing it for an analyte.

A species may be obtained from any suitable location, including from organisms, whole cells, cell preparations and cell-free compositions from any organism, tissue, cell, or environment. A species may be obtained from environmental samples, biopsies, aspirates, formalin fixed embedded tissues, air, agricultural samples, soil samples, petroleum samples, water samples, or dust samples. In some instances, a species may be obtained from bodily fluids which may include blood, urine, feces, serum, lymph, saliva, mucosal secretions, perspiration, central nervous system fluid, vaginal fluid, or semen. Species may also be obtained from manufactured products, such as cosmetics, foods, personal care products, and the like. Species may be the products of experimental manipulation including, recombinant cloning, polynucleotide amplification, polymerase chain reaction (PCR) amplification, purification methods (such as purification of genomic DNA or RNA), and synthesis reactions.

In some cases, a species may quantified by mass. A species may be provided in a mass of about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng, 1 µg, 5 µg, 10 µg, 15 µg, or 20 µg. A species may be provided in a mass of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng, 1 µg, 5 µg, 10 µg, 15 µg, or 20 µg. A species may be provided in a mass of less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng 1 µg, 5 µg, 10 µg, 15 µg, or 20 µg. A species may be provided in a mass ranging from about 1-10, 10-50, 50-100, 100-200, 200-1000, 1000-10000 ng, 1-5 or 1-20 µg. As described elsewhere in this disclosure, if a species is a polynucleotide, amplification may be used to increase the quantity of a polynucleotide.

Polynucleotides may also be quantified as "genome equivalents." A genome equivalent is an amount of polynucleotide equivalent to one haploid genome of an organism from which the target polynucleotide is derived. For example, a single diploid cell contains two genome equivalents of DNA. Polynucleotides may be provided in an amount ranging from about 1-10, 10-50, 50-100, 100-1000, 1000-10000, 10000-100000, or 100000-1000000 genome equivalents. Polynucleotides may be provided in an amount of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents. Polynucleotides may be provided in an amount less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents.

Polynucleotides may also be quantified by the amount of sequence coverage provided. The amount of sequence coverage refers to the average number of reads representing a given nucleotide in a reconstructed sequence. Generally, the greater the number of times a region is sequenced, the more accurate the sequence information obtained. Polynucleotides may be provided in an amount that provides a range of sequence coverage from about 0.1X-10X, 10-X-50X, 50X-100X, 100X-200X, or 200X-500X. Polynucleotides may be provided in an amount that provides at least about 0.1X, 0.2X, 0.3X, 0.4X, 0.5X, 0.6X, 0.7X, 0.8X, 0.9X, 1.0X, 5X, 10X, 25X, 50X, 100X, 125X, 150X, 175X, or 200X sequence coverage. Polynucleotides may be provided in an amount that provides less than about 0.2X, 0.3X, 0.4X, 0.5X, 0.6X, 0.7X, 0.8X, 0.9X, 1.0X, 5X, 10X, 25X, 50X, 100X, 125X, 150X, 175X, or 200X sequence coverage.

In some cases, species are introduced into a partition either before or after a particular step. For example, a lysis buffer reagent may be introduced into a partition following partitioning of a cellular sample into the partitions. In some cases, reagents and/or partitions comprising reagents are introduced sequentially such that different reactions or operations occur at different steps. The reagents (or partitions comprising reagents) may be also be loaded at steps interspersed with a reaction or operation step. For example, capsules comprising reagents for fragmenting molecules (e.g., nucleic acids) may be loaded into a well, followed by a fragmentation step, which may be followed by loading of capsules comprising reagents for ligating barcodes (or other unique identifiers, e.g., antibodies) and subsequent ligation of the barcodes to the fragmented molecules.

IV. PROCESSING OF ANALYTES AND OTHER SPECIES

In some cases, the methods, compositions, systems, devices, and kits of this disclosure may be used to process a sample containing a species, for example an analyte. Any suitable process can be performed.

a. Fragmentation of Target Polynucleotides

In some cases, the methods, compositions, systems, devices, and kits of this disclosure may be used for polynucleotide fragmentation. Fragmentation of polynucleotides is used as a step in a variety of methods, including polynucleotide sequencing. The size of the polynucleotide fragments, typically described in terms of length (quantified by the linear number of nucleotides per fragment), may vary depending on the source of the target polynucleotide, the method used for fragmentation, and the desired application. A single fragmentation step or a plurality of fragmentation steps may be used.

Fragments generated using the methods described herein may be about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides in length. Fragments generated using the methods described herein may be at least about 10, 20, 100, 200, 300, 400, 500, 1000, 5000, 10000, 100000, 250000, 500000, or more nucleotides in length. Fragments generated using the methods described herein may be less than about 10, 20, 100, 200, 300, 400, 500, 1000, 5000, 10000, 100000, 250000, 500000, nucleotides in length.

Fragments generated using the methods described herein may have a mean or median length of about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides. Fragments generated using the methods described herein may have a mean or median length of at least about 10, 20, 100, 200, 300, 400, 500, 1000, 5000, 10000, 100000, 250000, 500000, or more nucleotides. Fragments generated using the methods described herein may have a mean or median length of less than about 10, 20, 100, 200, 300, 400, 500, 1000, 5000, 10000, 100000, 250000, 500000, nucleotides.

Numerous fragmentation methods are known in the art. For example, fragmentation may be performed through physical, mechanical or enzymatic methods. Physical fragmentation may include exposing a target polynucleotide to heat or to UV light. Mechanical disruption may be used to mechanically shear a target polynucleotide into fragments of the desired range. Mechanical shearing may be accomplished through a number of methods known in the art, including repetitive pipetting of the target polynucleotide, sonication (e.g., using ultrasonic waves), cavitation and nebulization. Target polynucleotides may also be fragmented using enzymatic methods. In some cases, enzymatic digestion may be performed using enzymes such as using restriction enzymes.

While the methods of fragmentation described in the preceding paragraph, and in some paragraphs of the disclosure, are described with reference to "target" polynucleotides, this is not meant to be limiting, above or anywhere else in this disclosure. Any method of fragmentation described herein, or known in the art, can be applied to any polynucleotide used with the invention. In some cases, this polynucleotide may be a target polynucleotide, such as a genome. In other cases, this polynucleotide may be a fragment of a target polynucleotide which one wishes to further fragment. In still other cases, still further fragments may be still further fragmented. Any suitable polynucleotide may be fragmented according the methods described herein.

Restriction enzymes may be used to perform specific or non-specific fragmentation of target polynucleotides. The methods of the present disclosure may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide base pairs within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods of the present disclosure may comprise use of restriction enzymes that generate either sticky ends or blunt ends.

Restriction enzymes may recognize a variety of recognition sites in the target polynucleotide. Some restriction enzymes ("exact cutters") recognize only a single recognition site (e.g., GAATTC). Other restriction enzymes are more promiscuous, and recognize more than one recognition site, or a variety of recognition sites. Some enzymes cut at a single position within the recognition site, while others may cut at multiple positions. Some enzymes cut at the same position within the recognition site, while others cut at variable positions.

The present disclosure provides method of selecting one or more restriction enzymes to produce fragments of a desired length. Polynucleotide fragmentation may be simulated in silico, and the fragmentation may be optimized to obtain the greatest number or fraction of polynucleotide fragments within a particular size range, while minimizing the number or fraction of fragments within undesirable size ranges. Optimization algorithms may be applied to select a combination of two or more enzymes to produce the desired fragment sizes with the desired distribution of fragments quantities.

A polynucleotide may be exposed to two or more restriction enzymes simultaneously or sequentially. This may be accomplished by, for example, adding more than one restriction enzyme to a partition, or by adding one restriction enzyme to a partition, performing the digestion, deactivating the restriction enzyme (e.g., by heat treatment) and then adding a second restriction enzyme. Any suitable restriction enzyme may be used alone, or in combination, in the methods presented herein.

In some cases, a species is a restriction enzyme that is a "rare-cutter." The term "rare-cutter enzyme," as used herein, generally refers to an enzyme with a recognition site that occurs only rarely in a genome. The size of restriction fragments generated by cutting a hypothetical random genome with a restriction enzyme may be approximated by $4^N$, where N is the number of nucleotides in the recognition site of the enzyme. For example, an enzyme with a recognition site consisting of 7 nucleotides would cut a genome once every $4^7$ bp, producing fragments of about 16,384 bp. Generally rare-cutter enzymes have recognition sites comprising 6 or more nucleotides. For example, a rare cutter enzyme may have a recognition site comprising or consisting of 6, 7, 8, 9, 10, 11, 12, 13, 14, or 15 nucleotides. Examples of rare-cutter enzymes include NotI (GCGGCCGC), XmaIII (CGGCCG), SstII (CCGCGG), SalI (GTCGAC), NruI (TCGCGA), NheI (GCTAGC), Nb.BbvCI (CCTCAGC), BbvCI (CCTCAGC), AscI (GGCGCGCC), AsiSI (GCGATCGC), FseI (GGCCGGCC), PacI (TTAATTAA), PmeI (GTTTAAAC), SbfI (CCTGCAGG), SgrAI (CRCCGGYG), SwaI (ATTTAAAT), BspQI (GCTCTTC), SapI (GCTCTTC), SfiI (GGCCNNNNNGGCC), CspCI (CAANNNNNGTGG), AbsI (CCTCGAGG), CciNI (GCGGCCGC), FspAI (RTGCGCAY), MauBI (CGCGCGCG), MreI (CGCCGGCG), MssI (GTTTAAAC), PalAI (GGCGCGCC), RgaI (GCGATCGC), RigI (GGCCGGCC), SdaI (CCTGCAGG), SfaAI (GCGATCGC), SgfI (GCGATCGC), SgrDI (CGTCGACG), SgsI (GGCGCGCC), SmiI (ATTTAAAT), SrfI (GCCCGGGC), Sse2321 (CGCCGGCG), Sse83871 (CCTGCAGG), LguI (GCTCTTC), PciSI (GCTCTTC), AarI (CACCTGC), AjuI (GAANNNNNNNTTGG), AloI (GAACNNNNNNTCC), BarI (GAAGNNNNNNTAC), PpiI (GAACNNNNNCTC), PsrI (GAACNNNNNNTAC), and others.

In some cases, polynucleotides may be fragmented and barcoded at the same time. For example, a transposase (e.g., NEXTERA) may be used to fragment a polynucleotide and add a barcode to the polynucleotide.

b. Barcoding

Certain downstream applications, for example polynucleotide sequencing, may rely on the barcodes to identify the origin of a sequence and, for example, to assemble a larger sequence from sequenced fragments. Therefore, it may be desirable to add barcodes to polynucleotide fragments before sequencing. Barcodes may be of a variety of different formats, including polynucleotide barcodes. Depending upon the specific application, barcodes may be attached to polynucleotide fragments in a reversible or irreversible manner. Barcodes may also allow for identification and/or quantification of individual polynucleotide fragments during sequencing.

Barcodes may be loaded into partitions so that one or more barcodes are introduced into a particular partition. Each partition may contain a different set of barcodes. In some cases, each different set of barcodes may comprise a set of identical barcodes. This may be accomplished by directly dispensing the barcodes into the partitions, or by placing the barcodes within a partition within a partition.

The number of different barcodes or different sets of barcodes that are partitioned may vary depending upon, for example, the particular barcodes to be partitioned and/or the application. Different sets of barcodes may be, for example, sets of identical barcodes where the identical barcodes differ between each set. Or different sets of barcodes may be, for example, sets of different barcodes, where each set differs in its included barcodes. For example, about 1, 5, 10, 50, 100, 1000, 10000, 20,000, 30,000, 40,000, 50,000, 60,000, 70,000, 80,000, 90,000, 100,000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes or different sets of barcodes may be partitioned. In some examples, about 1-5, 5-10, 10-50, 50-100, 100-1000, 1000-10000, 10000-100000, 100000-1000000, 10000-1000000, 10000-10000000, or 10000-100000000 barcodes may be partitioned.

Barcodes may be partitioned at a particular density. For example, barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 barcodes per partition.

Barcodes may be partitioned such that identical barcodes are partitioned at a particular density. For example, identical barcodes may be partitioned so that each partition contains about 1, 5, 10, 50, 100, 1000, 10000, 20,000, 30,000, 40,000, 50,000, 60,000, 70,000, 80,000, 90,000, 100,000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more identical barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 identical barcodes per partition.

Barcodes may be partitioned such that different barcodes are partitioned at a particular density. For example, different barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 different barcodes per partition.

The number of partitions employed to partition barcodes may vary, for example, depending on the application and/or the number of different barcodes to be partitioned. For example, the number of partitions employed to partition barcodes may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000 or more. The number of partitions employed to partition barcodes may be at least about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000 or more. The number of partitions employed to partition barcodes may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions employed to partition barcodes may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

As described above, different barcodes or different sets of barcodes (e.g., each set comprising a plurality of identical barcodes or different barcodes) may be partitioned such that each partition comprises a different barcode or different barcode set. In some cases, each partition may comprise a different set of identical barcodes. Where different sets of identical barcodes are partitioned, the number of identical barcodes per partition may vary. For example, about 100,000 or more different sets of identical barcodes may be partitioned across about 100,000 or more different partitions, such that each partition comprises a different set of identical barcodes. In each partition, the number of identical barcodes per set of barcodes may be about 1,000,000 identical barcodes. In some cases, the number of different sets of barcodes may be equal to or substantially equal to the number of partitions. Any suitable number of different barcodes or different barcode sets (including numbers of different barcodes or different barcode sets to be partitioned described elsewhere herein), number of barcodes per partition (including numbers of barcodes per partition described elsewhere herein), and number of partitions (including numbers of partitions described elsewhere herein) may be combined to generate a diverse library of partitioned barcodes with high numbers of barcodes per partition. Thus, as will be appreciated, any of the above-described different numbers of barcodes may be provided with any of the above-described barcode densities per partition, and in any of the above-described numbers of partitions.

The barcodes may be loaded into the partitions at an expected or predicted ratio of barcodes per species to be barcoded (e.g., polynucleotide fragment, strand of polynucleotide, cell, etc.). In some cases, the barcodes are loaded into partitions such that more than about 1, 2, 3, 4, 5, 6, 7, 8, 9, 10, 20, 50, 100, 500, 1000, 5000, 10000, or 200000 barcodes are loaded per species. In some cases, the barcodes are loaded in the partitions so that less than about 1, 2, 3, 4, 5, 6, 7, 8, 9, 10, 20, 50, 100, 500, 1000, 5000, 10000, or 200000 barcodes are loaded per species. In some cases, the average number of barcodes loaded per species is less than, or greater than, about 0.0001, 0.001, 0.01, 0.1, 1, 2, 3, 4, 5, 6, 7, 8, 9, 10, 20, 50, 100, 500, 1000, 5000, 10000, or 200000 barcodes per species.

When more than one barcode is present per polynucleotide fragment, such barcodes may be copies of the same barcode, or multiple different barcodes. For example, the attachment process may be designed to attach multiple identical barcodes to a single polynucleotide fragment, or multiple different barcodes to the polynucleotide fragment.

The methods provided herein may comprise loading a partition with the reagents necessary for the attachment of barcodes to polynucleotide fragments. In the case of ligation reactions, reagents including restriction enzymes, ligase enzymes, buffers, adapters, barcodes and the like may be loaded into a partition. In the case barcoding by amplification, reagents including primers, DNA polymerases, DNTPs, buffers, barcodes and the like may be loaded into a partition. As described throughout this disclosure, these reagents may be loaded directly into the partition, or via another partition.

Barcodes may be ligated to a polynucleotide fragment using sticky or blunt ends. Barcoded polynucleotide fragments may also be generated by amplifying a polynucleotide fragment with primers comprising barcodes. As with any other species discussed in this disclosure, these modules may be contained within the same or different partitions, depending on the needs of assay or process.

Barcodes may be assembled combinatorially, from smaller components designed to assemble in a modular format. For example, three modules, 1A, 1B, and 1C may be combinatorially assembled to produce barcode 1ABC. Such combinatorial assembly may significantly reduce the cost of synthesizing a plurality of barcodes. For example, a combinatorial system consisting of 3 A modules, 3 B modules, and 3 C modules may generate 3*3*3=27 possible barcode sequences from only 9 modules.

In some cases, barcodes may be combinatorially assembled by mixing two oligonucleotides and hybridizing them to produce annealed or partially annealed oligonucleotides (e.g., forked adapters). These barcodes may comprise an overhang of one or more nucleotides, in order to facilitate ligation with polynucleotide fragments that are to be barcoded. In some cases, the 5' end of the antisense strand may be phosphorylated in order to ensure double-stranded ligation. Using this approach, different modules may be assembled by, for example, mixing oligonucleotides A and B, A and C, A and D, B and C, B, and D, and so on. The annealed oligonucleotides may also be synthesized as a single molecule with a hairpin loop that may be cut after ligation to the polynucleotide to be barcoded.

c. Amplification

In some cases, a polynucleotide is amplified during sample processing. This amplification may be performed in one or more of the partitions described in this disclosure. Amplification may be useful for a variety of purposes, including but not limited to generating multiple copies of polynucleotide sequences, addition of adapter sequences or barcodes to polynucleotides, mutation or error detection, producing higher quality samples for further downstream processing and the like.

An suitable amplification method may be utilized, including polymerase chain reaction (PCR), ligase chain reaction (LCR), helicase-dependent amplification, linear after the exponential PCR (LATE-PCR) asymmetric amplification, digital PCR, degenerate oligonucleotide primer PCR (DOP-PCR), primer extension pre-amplification PCR (PEP-PCR) and ligation mediated PCR, rolling circle amplification, multiple displacement amplification (MDA), and single primer isothermal linear amplification. In one example, MDA may be performed on a species contained within a partition. In some cases, this species is a whole chromosome from a cell.

V. STIMULI-RESPONSIVENESS

In some cases, stimuli may be used to trigger the release of a species from a partition. Generally, a stimulus may cause disruption of the structure of a partition, such as the wall of a well, a component of a spot, the stability of a droplet (e.g., a droplet in an emulsion), or the shell of a capsule. These stimuli are particularly useful in inducing a partition to release its contents. Because a partition may be contained within another partition, and each partition may be responsive (or not responsive) to different stimuli, stimuli-responsiveness may be employed to release the contents of one partition (e.g., a partition responsive to the stimulus) into another partition (e.g., a partition not responsive to that stimulus, or less responsive to that stimulus).

Figure 8A:
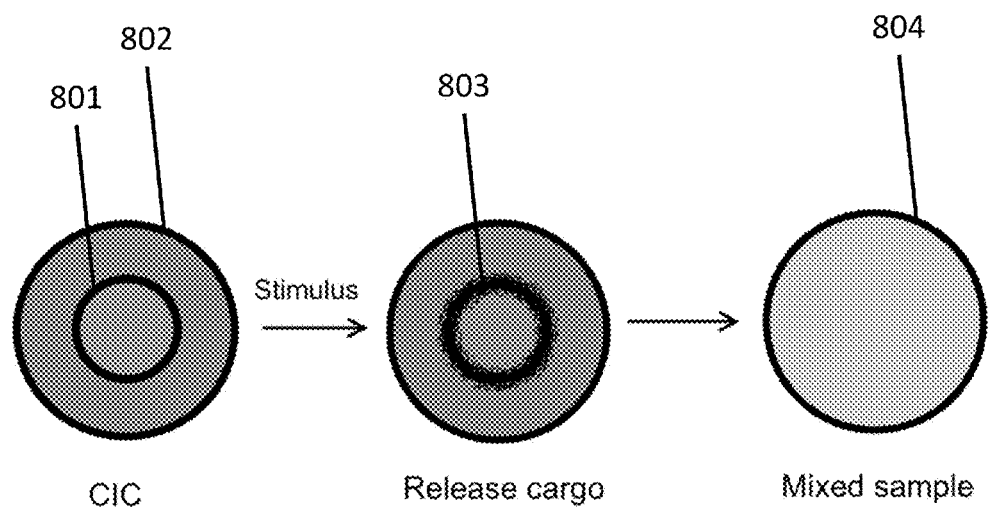
FIGS. 8A-8D are schematic examples of partition-in-partition configurations.

FIG. 8A shows one non-limiting example using a capsule as an exemplary partition. More specifically, FIG. 8A shows selective release of the contents of an inner capsule 801 into the contents of an outer capsule 802 by applying a stimulus that dissolves the inner capsule 803, resulting in a capsule containing a mixed sample 804.

Figure 8B:
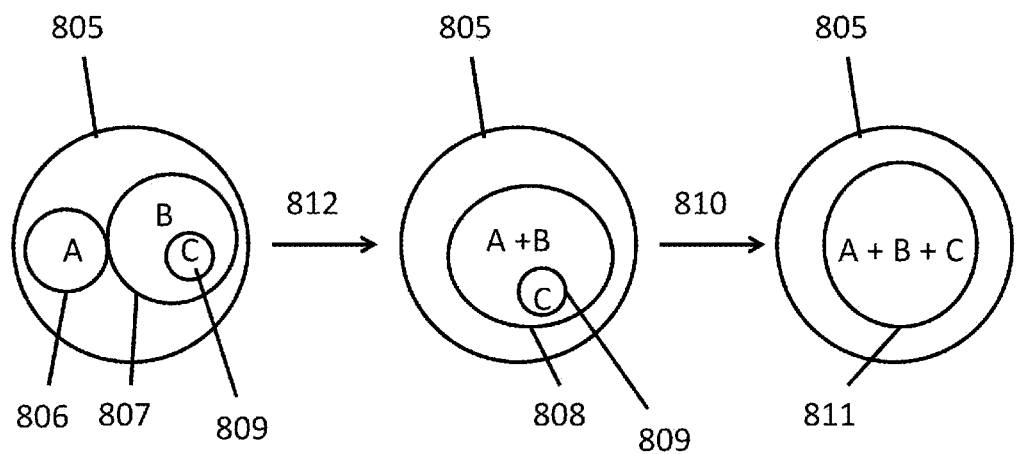

FIG. 8B shows another non-limiting example using a multiple partitions in a partition scheme. An outer partition 805 comprises inner partitions 806 and 807. Inner partition 806 comprises species A and inner partition 807 comprises species B along with its own inner partition 809 comprising species C. For example, the two inner partitions 806 and 807 may be droplets of an emulsion and outer partition 805 comprising the two droplets may be a well. In some cases, one or both of the two droplets may be a micelle Inner partition 809 may also be a droplet of an emulsion and may be capable of being dissolved or degraded by species A. In some cases species A may be chemical stimulus, such as, for example, a reducing agent (e.g., DTT, TCEP, etc.) capable of breaking disulfide bonds and inner partition 809 may comprise disulfide bonds (e.g., a gel bead comprising disulfide bonds) capable of being broken by species A.

Via diffusion or other means, inner partitions 806 and 807 may come into contact and fuse 812 together such that a new partition 808 can be generated comprising the combined contents of inner partitions 806 and 807 (e.g., species A+B+inner partition 809). The action 810 of species A on inner partition 809 can degrade or dissolve inner partition 809 such that the contents (e.g., species C) of inner partition 809 can be released into partition 808 to generate a new partition 811. Partition 811 comprises the combined contents of inner partitions 806, 807, and 809 (e.g., species A+B+C).

Figure 8C:
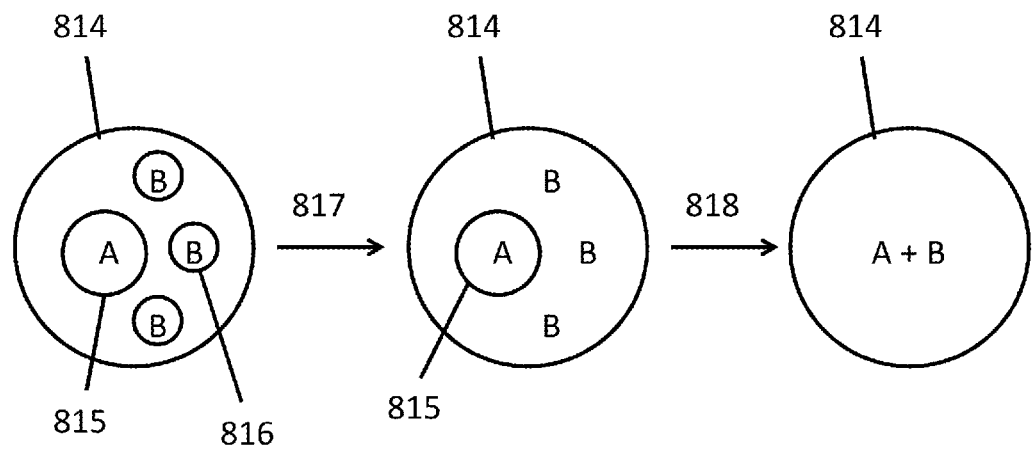

FIG. 8C shows another non-limiting example using a multiple partitions in a partition scheme. Outer partition 814 may comprise inner partition 815 and one or more inner partitions 816 (multiple inner partitions 816 are shown) and may be, for example, a droplet of an emulsion. Inner partition 815 comprises species A and inner partition 816 comprises species B. In some cases, species B may be a chemical stimulus capable of degrading or dissolving inner partition 815. Species B may be, for example, a reducing agent (e.g., DTT, TCEP, etc.) capable of breaking disulfide bonds and inner partition 815 may comprise disulfide bonds (e.g., a gel bead comprising disulfide bonds) capable of being dissolved or degraded by species B. Moreover, inner partition 816 may be heat sensitive (e.g., a paraffin or other wax bead) such that upon application of heat, species B can be released into the interior of outer partition 814.

Upon application of an appropriate stimulus 817 (e.g., heat), inner partitions 816 may be disrupted or degraded such that species B is released to the interior of outer partition 814. The action 818 of species B on inner partition 815 can degrade or dissolve inner partition 815 such that the contents of inner partition 815 can be released to the interior of outer partition 814. Outer partition 814 can then comprise the combined contents (e.g., species A+B) of inner partitions 815 and 816.

In another example, species B as described above with respect to FIG. 8C, may be a reagent necessary to start a reaction in the interior of outer partition 814, such as, for example, an amplification reaction. Upon degradation or disruption of inner partition 816 with the appropriate stimulus (e.g., heat), species B may be released to the interior of outer partition 814, and the desired reaction allowed to commence with or without the application of an additional stimulus.

Figure 8D:
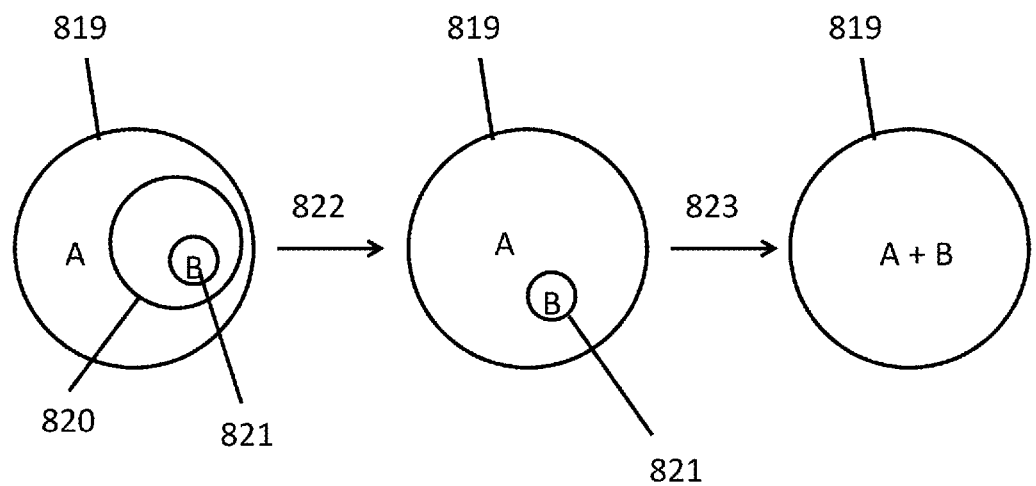

FIG. 8D shows another non-limiting example using a multiple partitions in a partition scheme. Outer partition 819 comprises species A and inner partition 820 and may be, for example, a droplet of an emulsion. Inner partition 820 can be impermeable to species A Inner partition 820 can comprise its own inner partition 821 which comprises species B Inner partition 820 may be sensitive to a stimulus such that when the stimulus is applied to inner partition 820, inner partition 820 is dissolved or degraded and inner partition 821 is released to the interior of outer partition 819. Inner partition 820 may be, for example, a microcapsule with a hardened shell that comprises, for example, a heat-sensitive shell that degrades or melts when heat is applied to inner partition 820. Inner partition 821 may be sensitive to species A, such that species A is capable of degrading or dissolving inner partition 821. For example, species A may be a reducing agent capable of breaking disulfide bonds and inner partition 821 may comprise a species comprising disulfide bonds (e.g., a gel bead comprising disulfide bonds) capable of being broken with species A.

Upon application of an appropriate stimulus 822 (e.g., heat), inner partition 820 may be disrupted or degraded such that inner partition 821 is released to the interior of outer partition 819. The action 823 of species A on inner partition 821 can degrade or dissolve inner partition 821 such that the contents of inner partition 821 (e.g., species B) can be released to the interior of outer partition 819. Outer partition 819 can then comprise the combined contents (e.g., species A+B) of inner partition 821 and outer partition 819.

Of course, the configuration shown in FIGS. 8A-8D are merely illustrative, and stimuli-responsiveness may be used to release the contents of any suitable partition into any other suitable partition, medium, or container (see, e.g., Table 1 for more specific examples of partitions within partitions).

Examples of stimuli that may be used include chemical stimuli, bulk changes, biological stimuli, light, thermal stimuli, magnetic stimuli, addition of a medium to a well, and any combination thereof, as described more fully below. (See, e.g., Esser-Kahn et al., (2011) *Macromolecules* 44: 5539-5553; Wang et al., (2009) *Chem Phys Chem* 10:2405-2409.)

a. Chemical Stimuli and Bulk Changes

Numerous chemical triggers may be used to trigger the disruption of partitions (e.g., Plunkett et al., Biomacromolecules, 2005, 6:632-637). Examples of these chemical changes may include, but are not limited to pH-mediated changes to the integrity of a component of a partition, disintegration of a component of a partition via chemical cleavage of crosslink bonds, and triggered depolymerization of a component of a partition. Bulk changes may also be used to trigger disruption of partitions.

A change in pH of a solution, such as a decrease in pH, may trigger disruption of a partition via a number of different mechanisms. The addition of acid may cause degradation or disassembly a portion of a partition through a variety of mechanisms. Addition of protons may disassemble cross-linking of polymers in a component of a partition, disrupt ionic or hydrogen bonds in a component of a partition, or create nanopores in a component of a partition to allow the inner contents to leak through to the exterior. A change in pH may also destabilize an emulsion, leading to release of the contents of the droplets.

In some examples, a partition is produced from materials that comprise acid-degradable chemical cross-linkers, such a ketals. A decrease in pH, particular to a pH lower than 5, may induce the ketal to convert to a ketone and two alcohols and facilitate disruption of the partition. In other examples, the partitions may be produced from materials comprising one or more polyelectrolytes that are pH sensitive. A decrease in pH may disrupt the ionic- or hydrogen-bonding interactions of such partitions, or create nanopores therein. In some cases, partitions made from materials comprising polyelectrolytes comprise a charged, gel-based core that expands and contracts upon a change of pH.

Disruption of cross-linked materials comprising a partition can be accomplished through a number of mechanisms. In some examples, a partition can be contacted with various chemicals that induce oxidation, reduction or other chemical changes. In some cases, a reducing agent, such as beta-mercaptoethanol, can be used, such that disulfide bonds of a partition are disrupted. In addition, enzymes may be added to cleave peptide bonds in materials forming a partition, thereby resulting in a loss of integrity of the partition.

Depolymerization can also be used to disrupt partitions. A chemical trigger may be added to facilitate the removal of a protecting head group. For example, the trigger may cause removal of a head group of a carbonate ester or carbamate within a polymer, which in turn causes depolymerization and release of species from the inside of a partition.

In yet another example, a chemical trigger may comprise an osmotic trigger, whereby a change in ion or solute concentration in a solution induces swelling of a material used to make a partition. Swelling may cause a buildup of internal pressure such that a partition ruptures to release its contents. Swelling may also cause an increase in the pore size of the material, allowing species contained within the partition to diffuse out, and vice versa.

A partition may also be made to release its contents via bulk or physical changes, such as pressure induced rupture, melting, or changes in porosity.

b. Biological Stimuli

Biological stimuli may also be used to trigger disruption of partitions. Generally, biological triggers resemble chemical triggers, but many examples use biomolecules, or molecules commonly found in living systems such as enzymes, peptides, saccharides, fatty acids, nucleic acids and the like. For example, partitions may be made from materials comprising polymers with peptide cross-links that are sensitive to cleavage by specific proteases. More specifically, one example may comprise a partition made from materials comprising GFLGK peptide cross links. Upon addition of a biological trigger such as the protease Cathepsin B, the peptide cross links of the shell well are cleaved and the contents of the capsule are released. In other cases, the proteases may be heat-activated. In another example, partitions comprise a component comprising cellulose. Addition of the hydrolytic enzyme chitosan serves as biologic trigger for cleavage of cellulosic bonds, depolymerization of component of the partition comprising chitosan, and release of its inner contents.

c. Thermal Stimuli

Partitions may also be induced to release their contents upon the application of a thermal stimulus. A change in temperature can cause a variety changes to a partition. A change in heat may cause melting of a partition such that a portion of the partition disintegrates, or disruption of an emulsion. In other cases, heat may increase the internal pressure of the inner components of a partition such that the partition ruptures or explodes. In still other cases, heat may transform a partition into a shrunken dehydrated state. Heat may also act upon heat-sensitive polymers used as materials to construct partitions.

In one example, a partition is made from materials comprising a thermo-sensitive hydrogel. Upon the application of heat, such as a temperature above 35 C, the hydrogel material shrinks. The sudden shrinkage of the material increases the pressure and ruptures the partition.

In some cases, a material used to produce a partition may comprise a diblock polymer, or a mixture of two polymers, with different heat sensitivities. One polymer may be particularly likely to shrink after the application of heat, while the other is more heat-stable. When heat is applied to such shell wall, the heat-sensitive polymer may shrink, while the other remains intact, causing a pore to form. In still other cases, a material used to produce a partition may comprise magnetic nanoparticles. Exposure to a magnetic field may cause the generation of heat, leading to rupture of the partition.

d. Magnetic Stimuli

Inclusion of magnetic nanoparticles in a material used to produce a partition may allow triggered rupture of the partition, as described above, as well as enable guidance of these partitions to other partitions (e.g., guidance of capsules to wells in an array). In one example, incorporation of $Fe_3O_4$ nanoparticles into materials used to produce partitions triggers rupture in the presence of an oscillating magnetic field stimulus.

e. Electrical and Light Stimuli

A partition may also be disrupted as the result of electrical stimulation. Similar to the magnetic particles described in the previous section, electrically sensitive particles can allow for both triggered rupture of partitions, as well as other functions such as alignment in an electric field or redox reactions. In one example, partitions made from materials comprising electrically sensitive material are aligned in an electric field such that release of inner reagents can be controlled. In other examples, electric fields may induce redox reactions within a partition that may increase porosity.

A light stimulus may also be used to disrupt the partitions. Numerous light triggers are possible and may include systems that use various molecules such as nanoparticles and chromophores capable of absorbing photons of specific ranges of wavelengths. For example, metal oxide coatings can be used to produce certain partitions. UV irradiation of partitions coated with SiO2/TiO2 may result in disintegration of the partition wall. In yet another example, photo switchable materials such as azobenzene groups may be incorporated in the materials used to produce the partitions. Upon the application of UV or visible light, chemicals such as these undergo a reversible cis-to-trans isomerization upon absorption of photons. In this aspect, incorporation of photo switches results in disintegration of a portion of a partition, or an increase in porosity of a portion of a partition.

f. Application of Stimuli

The devices, methods, compositions, systems, and kits of this disclosure may be used in combination with any apparatus or device that provides such trigger or stimulus. For example, if the stimulus is thermal, a device may be used in combination with a heated or thermally controlled plate, which allows heating of the wells and may induce the rupture of capsules. Any of a number of methods of heat transfer may be used for thermal stimuli, including but not limited to applying heat by radiative heat transfer, convective heat transfer, or conductive heat transfer. In other cases, if the stimulus is a biological enzyme, the enzyme may be injected into a device such that it is deposited into each well. In another aspect, if the stimulus is a magnetic or electric field, a device may be used in combination with a magnetic or electric plate.

VI. APPLICATIONS a. Polynucleotide Sequencing

Generally, the methods and compositions provided herein are useful for preparation of polynucleotide fragments for downstream applications such as sequencing. Sequencing may be performed by any available technique. For example, sequencing may be performed by the classic Sanger sequencing method. Sequencing methods may also include: high-throughput sequencing, pyrosequencing, sequencing-by-synthesis, single-molecule sequencing, nanopore sequencing, sequencing-by-ligation, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, SMRT sequencing (Pacific Biosciences) Maxim-Gilbert sequencing, primer walking, and any other sequencing methods known in the art.

In some cases varying numbers of fragments are sequenced. For example, in some cases about 30%-90% of the fragments are sequenced. In some cases, about 35%-85%, 40%-80%, 45%-75%, 50%-70%, 55%-65%, or 50%-60% of the fragments are sequenced. In some cases, at least about 30%, 40%, 50%, 60%, 70%, 80%, or 90% of the fragments are sequenced. In some cases less than about 30%, 40%, 50%, 60%, 70%, 80%, or 90% of the fragments are sequenced.

In some cases sequences from fragments are assembled to provide sequence information for a contiguous region of the original target polynucleotide that is longer than the individual sequence reads. Individual sequence reads may be about 10-50, 50-100, 100-200, 200-300, 300-400, or more nucleotides in length.

The identities of the barcode tags may serve to order the sequence reads from individual fragments as well as to differentiate between haplotypes. For example, during the partitioning of individual fragments, parental polynucleotide fragments may separated into different partitions. With an increase in the number of partitions, the likelihood of a fragment from both a maternal and paternal haplotype contained in the same partition becomes negligibly small. Thus, sequence reads from fragments in the same partition may be assembled and ordered.

b. Polynucleotide Phasing

This disclosure also provides methods and compositions to prepare polynucleotide fragments in such a manner that may enable phasing or linkage information to be generated. Such information may allow for the detection of linked genetic variations in sequences, including genetic variations (e.g., SNPs, mutations, indels, copy number variations, transversions, translocations, inversions, etc.) that are separated by long stretches of polynucleotides. The term "indel" refers to a mutation resulting in a colocalized insertion and deletion and a net gain or loss in nucleotides. A "microindel" is an indel that results in a net gain or loss of 1 to 50 nucleotides. These variations may exist in either a cis or trans relationship. In a cis relationship, two or more genetic variations exist in the same polynucleotide or strand. In a trans relationship, two or more genetic variations exist on multiple polynucleotide molecules or strands.

Methods provided herein may be used to determine polynucleotide phasing. For example, a polynucleotide sample (e.g., a polynucleotide that spans a given locus or loci) may be partitioned such that at most one molecule of polynucleotide is present per partition. The polynucleotide may then be fragmented, barcoded, and sequenced. The sequences may be examined for genetic variation. The detection of genetic variations in the same sequence tagged with two different bar codes may indicate that the two genetic variations are derived from two separate strands of DNA, reflecting a trans relationship. Conversely, the detection of two different genetic variations tagged with the same bar codes may indicate that the two genetic variations are from the same strand of DNA, reflecting a cis relationship.

Phase information may be important for the characterization of a polynucleotide fragment, particularly if the polynucleotide fragment is derived from a subject at risk of, having, or suspected of a having a particular disease or disorder (e.g., hereditary recessive disease such as cystic fibrosis, cancer, etc.). The information may be able to distinguish between the following possibilities: (1) two genetic variations within the same gene on the same strand of DNA and (2) two genetic variations within the same gene but located on separate strands of DNA. Possibility (1) may indicate that one copy of the gene is normal and the individual is free of the disease, while possibility (2) may indicate that the individual has or will develop the disease, particularly if the two genetic variations are damaging to the function of the gene when present within the same gene copy. Similarly, the phasing information may also be able to distinguish between the following possibilities: (1) two genetic variations, each within a different gene on the same strand of DNA and (2) two genetic variations, each within a different gene but located on separate strands of DNA.

c. Sequencing Polynucleotides from Small Numbers of Cells

Methods provided herein may also be used to prepare polynucleotide contained within cells in a manner that enables cell-specific information to be obtained. The methods enable detection of genetic variations (e.g., SNPs, mutations, indels, copy number variations, transversions, translocations, inversions, etc.) from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method comprises partitioning a cellular sample (or crude cell extract) such that at most one cell (or extract of one cell) is present per partition, lysing the cells, fragmenting the polynucleotides contained within the cells by any of the methods described herein, attaching the fragmented polynucleotides to barcodes, pooling, and sequencing.

As described elsewhere herein, the barcodes and other reagents may be contained within a partition (e.g., a capsule). These capsules may be loaded into another partition (e.g., a well) before, after, or concurrently with the loading of the cell, such that each cell is contacted with a different capsule. This technique may be used to attach a unique barcode to polynucleotides obtained from each cell. The resulting tagged polynucleotides may then be pooled and sequenced, and the barcodes may be used to trace the origin of the polynucleotides. For example, polynucleotides with identical barcodes may be determined to originate from the same cell, while polynucleotides with different barcodes may be determined to originate from different cells.

The methods described herein may be used to detect the distribution of oncogenic mutations across a population of cancerous tumor cells. For example, some tumor cells may have a mutation, or amplification, of an oncogene (e.g., HER2, BRAF, EGFR, KRAS) in both alleles (homozygous), others may have a mutation in one allele (heterozygous), and still others may have no mutation (wild-type). The methods described herein may be used to detect these differences, and also to quantify the relative numbers of homozygous, heterozygous, and wild-type cells. Such information may be used, for example, to stage a particular cancer and/or to monitor the progression of the cancer and its treatment over time.

In some examples, this disclosure provides methods of identifying mutations in two different oncogenes (e.g., KRAS and EGFR). If the same cell comprises genes with both mutations, this may indicate a more aggressive form of cancer. In contrast, if the mutations are located in two different cells, this may indicate that the cancer is more benign, or less advanced.

d. Analysis of Gene Expression

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

Cells may be placed directly into a partition (e.g., a microwell) and lysed. After lysis, the methods of the invention may be used to fragment and barcode the polynucleotides of the cell for sequencing. Polynucleotides may also be extracted from cells prior to introducing them into a partition used in a method of the invention. Reverse transcription of mRNA may be performed in a partition described herein, or outside of such a partition. Sequencing cDNA may provide an indication of the abundance of a particular transcript in a particular cell over time, or after exposure to a particular condition.

The methods presented above provide several advantages over current polynucleotide processing methods. First, inter-operator variability is greatly reduced. Second, the methods may be carried out in microfluidic devices, which have a low cost and can be easily fabricated. Third, the controlled fragmentation of the target polynucleotides allows the user to produce polynucleotide fragments with a defined and appropriate length. This aids in partitioning the polynucleotides and also reduces the amount of sequence information loss due to the present of overly-large fragments. The methods and systems also provide a facile workflow that maintains the integrity of the processed polynucleotide. Additionally, the use of restriction enzymes enables the user to create DNA overhangs ("sticky ends") that may be designed for compatibility with adapters and/or barcodes.

e. Partitioning of Polynucleotides, Such as Chromosomes, from Cells

In one example the methods, compositions, systems, devices, and kits provided in this disclosure may be used to partition polynucleotides, including whole chromosomes, from cells. In one example, a single cell or a plurality of cells (e.g., 2, 10, 50, 100, 1000, 10000, 25000, 50000, 100000, 500000, 1000000, or more cells) is loaded into a vessel with lysis buffer and proteinase K, and incubated for a specified period of time. Utilization of a plurality of cells will enable polynucleotide phasing, for example, by partitioning each polynucleotide to be analyzed in its own partition.

After incubation, the cell lysate is partitioned, for example by flow focusing the cell lysate into a capsule. If phasing is to be performed, flow focusing is performed such that each capsule comprises only a single analyte (e.g., a single chromosome), or only a single copy of any particular chromosome (e.g., one copy of a first chromosome and one copy of a second chromosome). In some cases, a plurality of chromosomes may be encapsulated within the same capsule, so long as the chromosomes are not the same chromosome. The encapsulation is performed under gentle flow, to minimize shearing of the polynucleotides. The capsule may be porous, to allow washing of the contents of the capsule, and introduction of reagents into the capsule, while maintaining the polynucleotides (e.g., chromosomes) within the capsules. The encapsulated polynucleotides (e.g., chromosomes) may then be processed according to any of the methods provided in this disclosure, or known in the art. The capsule shells protect the encapsulated polynucleotides (e.g., chromosomes) from shearing and further degradation. Of course, this method can also be applied to any other cellular component.

As described above, the capsule shell may be used to protect a polynucleotide from shearing. However, a capsule may also be used as a partition to enable compartmentalized shearing of a polynucleotide or other analyte. For example, in some cases a polynucleotide may be encapsulated within a capsule and then subject to ultrasonic shear, or any other suitable shearing. The capsule shell may be configured to remain intact under the shear, while the encapsulated polynucleotide may be sheared, but will remain within the capsule. In some cases, a hydrogel droplet may be used to accomplish the same end.

VIII. KITS

In some cases, this disclosure provides kits comprising reagents for the generation of partitions. The kit may comprise any suitable reagents and instructions for the generation of partitions and partitions within partitions.

In one example, a kit comprises reagents for generating capsules within droplets in an emulsion. For example, a kit may comprise reagents for generating capsules, reagents for generating an emulsion, and instructions for introducing the capsules into the droplets of the emulsion. As specified throughout this disclosure, any suitable species may be incorporated into the droplets and/or into the capsule. A kit of this disclosure may also provide any of these species. Similarly, as described throughout the disclosure, the capsule may be designed to release its contents into the droplets of the emulsion upon the application of a stimulus.

In another example, a kit comprises reagents for generating capsules within capsules. For example, a kit may comprise reagents for generating inner capsules, reagents for generating outer capsules, and instructions for generating capsules within capsules. As specified throughout this disclosure, any suitable species may be incorporated into the inner and/or outer capsules. A kit of this disclosure may also provide any of these species. Similarly, as described throughout the disclosure, the inner capsule may be designed to release its contents into the outer capsule upon the application of a stimulus.

IX. DEVICES

In some cases, this disclosure provides devices comprising partitions for the processing of analytes. A device may be a microwell array, or a microspot array, as described elsewhere in this disclosure. A device may formed in a manner that it comprises any suitable partition. In some cases, a device comprises a plurality of wells, or a plurality of spots. Of course, any partition in a device may also hold other partitions, such as a capsule, a droplet in an emulsion, and the like.

A device may be formed from any suitable material. In some examples, a device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases, a device comprises channels for the flow of fluids into and between partitions. Any suitable channels may be used. A device may comprise a fluid inlet and a fluid outlet. The inlet and outlet may be attached to liquid handling devices to introduce species into the device. The device may be sealed, before or after introduction of any species.

Materials that are hydrophilic and/or hydrophobic may be used in different parts of the device. For example, in some cases a device of this disclosure comprises a partition with an interior surface comprising a hydrophilic material. In some cases a surface exterior to the partitions comprises a hydrophobic material. In some cases, a fluid flow path is coated with a hydrophobic or hydrophilic material.

As will be appreciated, the instant disclosure provides for the use of any of the compositions, methods, devices, and kits described herein for a particular use or purpose, including the various applications, uses, and purposes described herein. For example, the disclosure provides for the use of the compositions, methods, devices, and kits described herein, in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, in circulating tumor cell (CTC) sequencing, in polynucleotide phasing, in sequencing polynucleotides from small numbers of cells, in analyzing gene expression, in partitioning polynucleotides from cells, in a combination thereof, and in any other application, method, process or use described herein.

EXAMPLES

Example 1: Production of Capsules by Flow Focusing

Figure 9A:
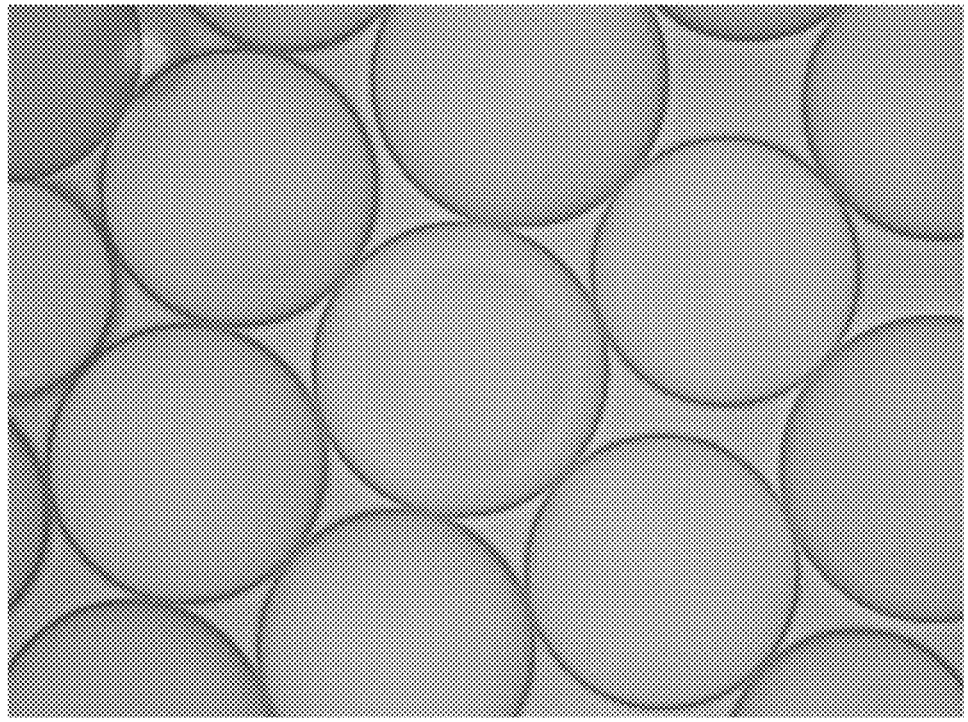
FIGS. 9A-B provide micrographs of capsules formed as described in Example 1.

Capsules were produced according to the method illustrated in FIG. 5 and the corresponding description of FIG. 5. The first fluid 501 was an aqueous fluid that contained 8% (w/v) N-isopropylacrylamide, 0.5% (w/v) PLURONIC F67, 2.5% (w/v) ammonium persulfate, and 1% (w/v) N,N'-methylenebisacrylamide. The second fluid 502 was a fluorous oil (HFE-7500) fluid that contained 2% (w/v) KRYTOX FSH and 1% (v/v) N,N,N,N-tetramethylethylene diamine. The T-junction was 100 microns in width, in either direction. The flow rate was adjusted to maintain an oil to aqueous ratio of 2:1 (20 uL/min and 10 uLmin, respectively). The resulting capsules are shown in FIG. 9A. The shells of the capsules are clearly visible as dark layers surrounding the interior. The size of the capsules is approximately 120 um.

Figure 9B:
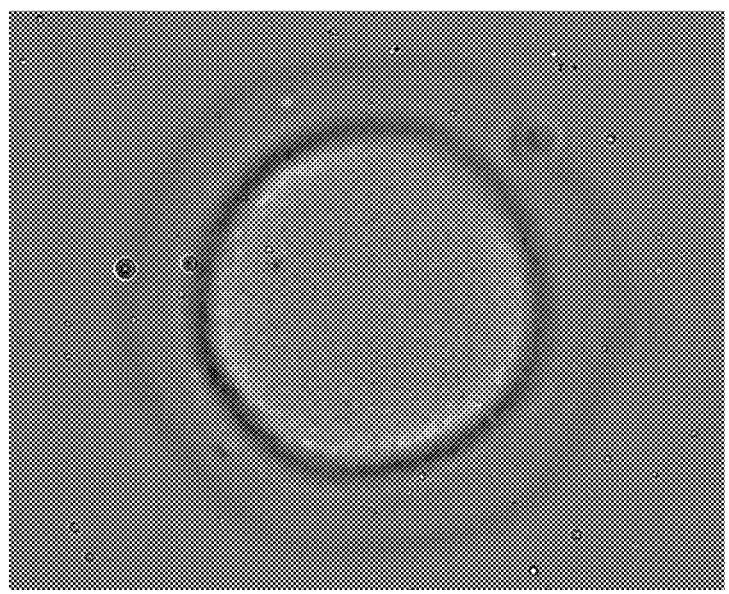

The capsules were washed and resuspended in water. FIG. 9B shows a micrograph of a single capsule, indicating that the integrity of the capsules is maintained during washing and resuspension.

Example 2: Production of Capsules in Batch

Figure 10:
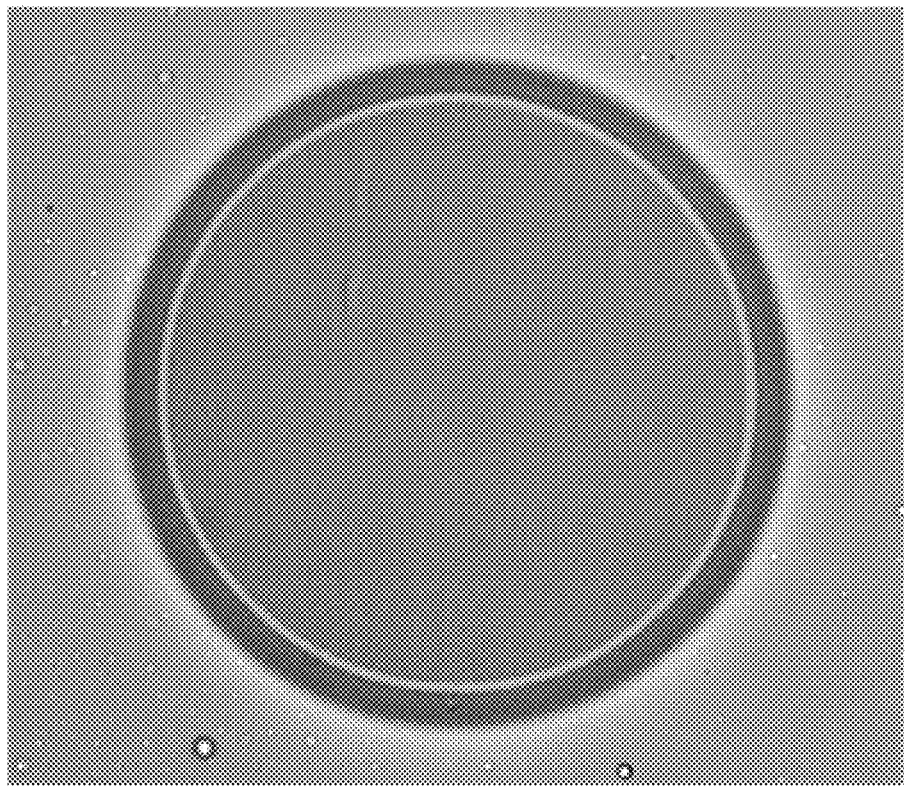
FIG. 10 provides a micrograph of a capsule formed as described in Example 2.

Capsules were produced according to the method illustrated in FIG. 7 and the corresponding description of FIG. 7. The first capsule precursors 701 contained 8% (w/v) N-isopropylacrylamide, 0.5% (w/v) PLURONIC F67, 2.5% (w/v) ammonium persulfate, and 1% (w/v) N,N'-methylenebisacrylamide stabilized by 2% (w/v) KRYTOX FSL in HFE7500. N,N,N, N-tetramethylethylene diamine was added to the medium containing the capsule precursors, at a concentration of 2% (w/v). A micrograph of a resulting capsule is shown in FIG. 10. The shell of the capsules is clearly visible as dark layers surrounding the interior. The size of the capsules is approximately 120 microns.

Example 3: Thermally-Responsive Capsules

Figure 11:
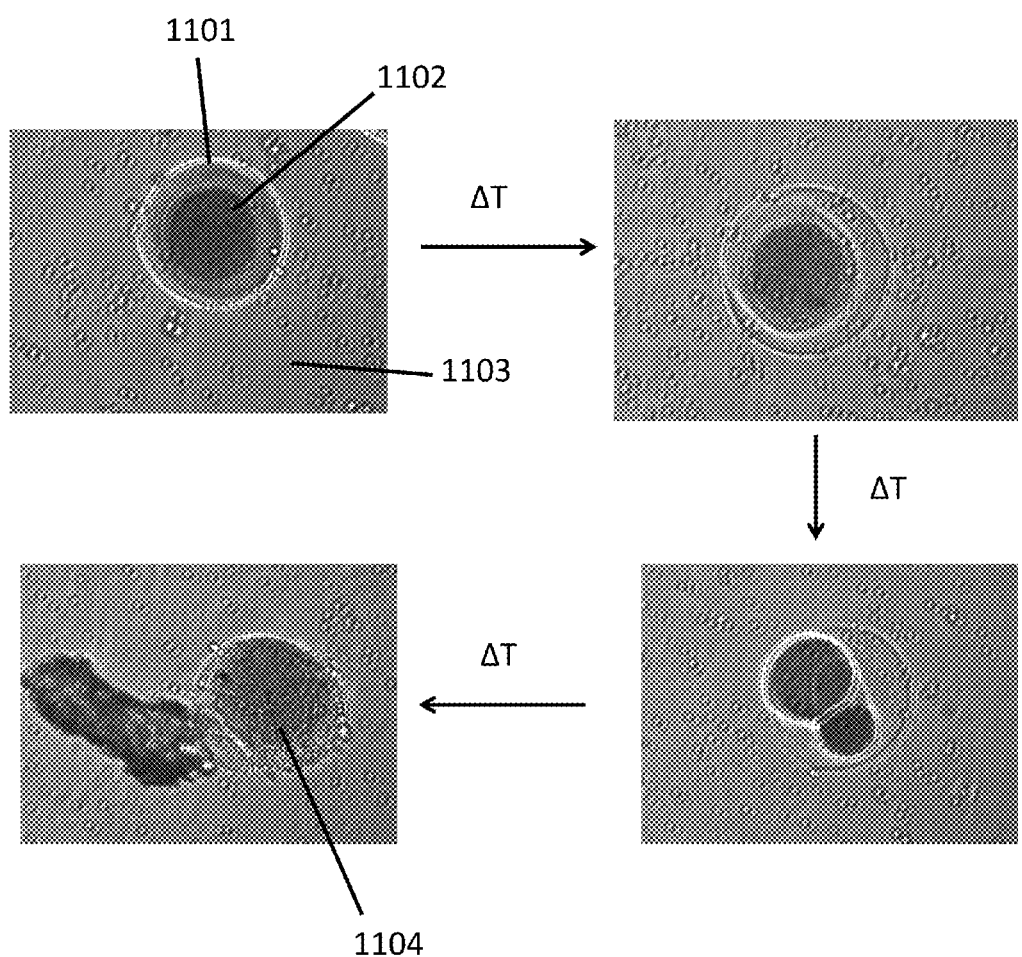
FIG. 11 provides micrographs of temperature-responsive capsules formed as described in Example 3.

Capsules were produced according to the method illustrated in FIG. 7 and the corresponding description of FIG. 7. The capsule shell wall was produced from N-isopropylacrylamide, a polymer that shrinks at a temperature above 32° C. With reference to FIG. 11, the capsules were made from a shell comprising the thermally responsive polymer 1101 and contained an aqueous interior 1102. The capsules were suspended in a oil phase 1103. Upon raising the temperature above 32° C. ($\Delta T$), the polymer in the capsule shell shrinks, leading to bursting of the capsule and release of the aqueous phase 1102 within the capsule directly into the surrounding oil phase 1103. The empty capsule shell 1104 is visible.

Example 4: Chemically-Responsive Capsules

Capsules were produced according to the method illustrated in FIG. 7 and the corresponding description of FIG. 7. The capsule shell wall was produced from a polymer comprising disulfide cross-links, which were dissolved after exposure to dithiothreitol (DTT). FIG. 12 shows selective dissolution of a capsule comprising disulfide cross-links after exposure to a medium containing 0.1M of DTT. The intact capsule 1201 was made with a shell comprising disulfide crosslinks. After 12.5 minutes of exposure to 0.1M DTT, the capsule shell dissolves, releasing the contents of the capsule, as shown in 1202. The appearance of the capsule at 2.5 minutes and 7.5 minutes is shown in 1203 and 1204, respectively.

Example 5: Examples of Configurations of Partitions

Many examples of different configurations of partitions are provided throughout this disclosure. FIG. 13 illustrates additional examples of configurations of partitions. In FIG. 13, the letters "A", "B", and "C" represent polynucleotide barcodes. The letter "S" represents an analyte (e.g., a sample). The letter "Z" represents another species, such as reagents that may be used to attach a barcode to a polynucleotide analyte. These configurations are in no way meant to be limiting and are provided only for the purposes of further illustrating certain embodiments of the invention. As described throughout this disclosure, any suitable configuration of any species (including species that are barcodes, analytes, and reagents) may be used. As described elsewhere in this disclosure, species may be introduced into capsules and droplets using any suitable method. Examples of suitable methods include flow focusing and picoinjection.

Figure 13A:
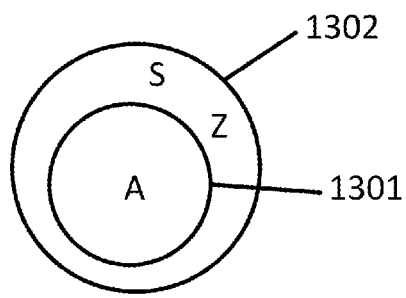
FIGS. 13A-E provide schematic examples of certain configurations of partitions, as described in Example 5.

The configuration of FIG. 13A is produced, using the methods described in this disclosure. With reference to FIG. 13A, an inner capsule or droplet of an emulsion 1301 comprising a barcode (A) is depicted. The inner capsule or droplet of an emulsion 1301 is contained within a partition 1302 that may be an outer capsule or a droplet of an emulsion. The medium between the inner capsule or droplet of an emulsion 1301 and the outer capsule or droplet of an emulsion 1302 comprises an analyte (S) and another species (Z) (e.g., a ligase, polymerase, etc.) for attaching the barcode (A) to the analyte (S). Using the methods described in this disclosure, the inner capsule or droplet of an emulsion 1301 can be induced to release its contents into the outer capsule or droplet of an emulsion 1302 in response to a stimulus, causing mixing of A, S, and Z.

Figure 13B:
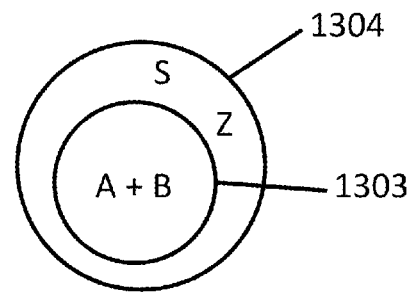

The configuration of FIG. 13B is produced, using the methods described in this disclosure. With reference to FIG. 13B, an inner capsule or droplet of an emulsion 1303 comprising two modular components of a barcode (A+B) is depicted. The inner capsule or droplet of an emulsion 1303 is contained within a partition 1304 that may be an outer capsule or droplet of an emulsion. The medium between the inner capsule or droplet of an emulsion 1303 and the outer capsule or droplet of an emulsion 1304 comprises an analyte (S) and another species (Z) (e.g., a ligase, polymerase, etc.) for attaching the barcode (A) to the analyte (S). The other species (Z) may also be used to assemble the two modular components of the barcode (A+B) and add the assembled barcode to the analyte (S), for example in a single ligation step. Using the methods described in this disclosure, the inner capsule or droplet of an emulsion 1303 can be induced to release its contents into the outer capsule or droplet of an emulsion 1304 in response to a stimulus, causing mixing of A, B, S, and Z.

Figure 13C:
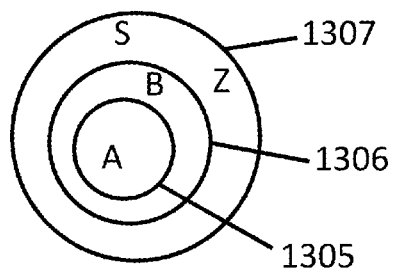

The configuration of FIG. 13C is produced, using the methods described in this disclosure. With reference to FIG. 13C, an inner capsule or droplet of an emulsion 1305 comprising a first modular component of a barcode (A) is depicted. The inner capsule or droplet of an emulsion 1305 is contained within a partition 1306 that may be an intermediate capsule or a droplet of an emulsion. The medium between the inner capsule or droplet of an emulsion 1305 and the intermediate capsule or droplet of an emulsion 1306 comprises a second modular component of a barcode (B). The intermediate capsule or droplet of an emulsion 1306 is contained within a partition 1307 that may be an outer capsule or droplet of an emulsion. The medium between the intermediate capsule or droplet of an emulsion 1306 and the outer capsule or droplet of an emulsion 1307 comprises an analyte (S) and another species (Z), each of which may be used as described above. Using the methods described in this disclosure, the inner capsule or droplet of an emulsion 1305 can be induced to release its contents into the intermediate capsule or droplet of an emulsion 1306 in response to a stimulus, causing mixing of A and B. Similarly, the intermediate capsule or droplet of an emulsion 1306 can be induced to release its contents into the outer capsule or droplet of an emulsion 1307, causing mixing of A, B, S, and Z (if the contents of 1305 have been released) or B, S, and Z (if the contents of 1305 have not been released).

Figure 13D:
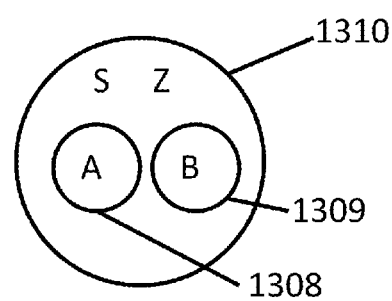

The configuration of FIG. 13D is produced, using the methods described in this disclosure. With reference to FIG. 13D, a first inner capsule or droplet of an emulsion 1308 comprises a first modular component of a barcode (A) and a second inner capsule or droplet of an emulsion 1309 comprises a second modular component of a barcode (B). The first and second inner capsules or droplets of an emulsion (1308 and 1309) are contained within a partition 1310 that may be an outer capsule or droplet of an emulsion. The medium between the first and second inner capsules or droplets of an emulsion (1308 and 1309) and the outer capsule or droplet of an emulsion 1310 comprises an analyte (S) and another species (Z), each of which may be used as described above. Using the methods described in this disclosure, either or both of the first 1308 or second 1309 inner capsules or droplets of an emulsion can be induced to release their contents into the outer capsule or droplet of an emulsion 1310 in response to a stimulus, causing mixing of A and/or B (depending on which inner capsules have released their contents), S, and Z.

Figure 13E:
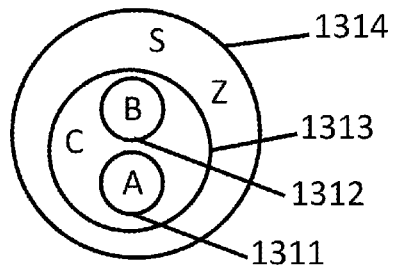

The configuration of FIG. 13E is produced, using the methods described in this disclosure. With reference to FIG. 13E, a first inner capsule or droplet of an emulsion 1311 comprises a first modular component of a barcode (A) and a second inner capsule or droplet of an emulsion 1312 comprises a second modular component of a barcode (B). The first and second inner capsules or droplets of an emulsion (1311 and 1312) are contained within an intermediate capsule or droplet of an emulsion 1313. The medium between the first and second inner capsules or droplets of an emulsion (1311 and 1312) and the intermediate capsule or droplet of an emulsion 1313 comprises a third modular component of a barcode (C). The intermediate capsule or droplet of an emulsion 1313 is contained within an outer capsule or droplet of an emulsion 1314. The medium between the intermediate capsule or droplet of an emulsion 1313 and the outer capsule or droplet of an emulsion 1314 comprises an analyte (S) and another species (Z), each of which may be used as described above. Using the methods described in this disclosure, either or both of the first 1311 or second 1312 inner capsules or droplets of an emulsion can be induced to release their contents into the intermediate capsule or droplet of an emulsion 1313 in response to a stimulus, causing mixing of A and/or B (depending on which inner capsules have released their contents) with C. Similarly, the intermediate capsule or droplet of an emulsion 1313 can be induced to release its contents into the outer capsule or droplet of an emulsion 1314, causing mixing of A, B, C, S, and Z, depending on which contents of 1311 and 1312 have been released.

Example 6: Spotting of Species within Wells

Figure 14:
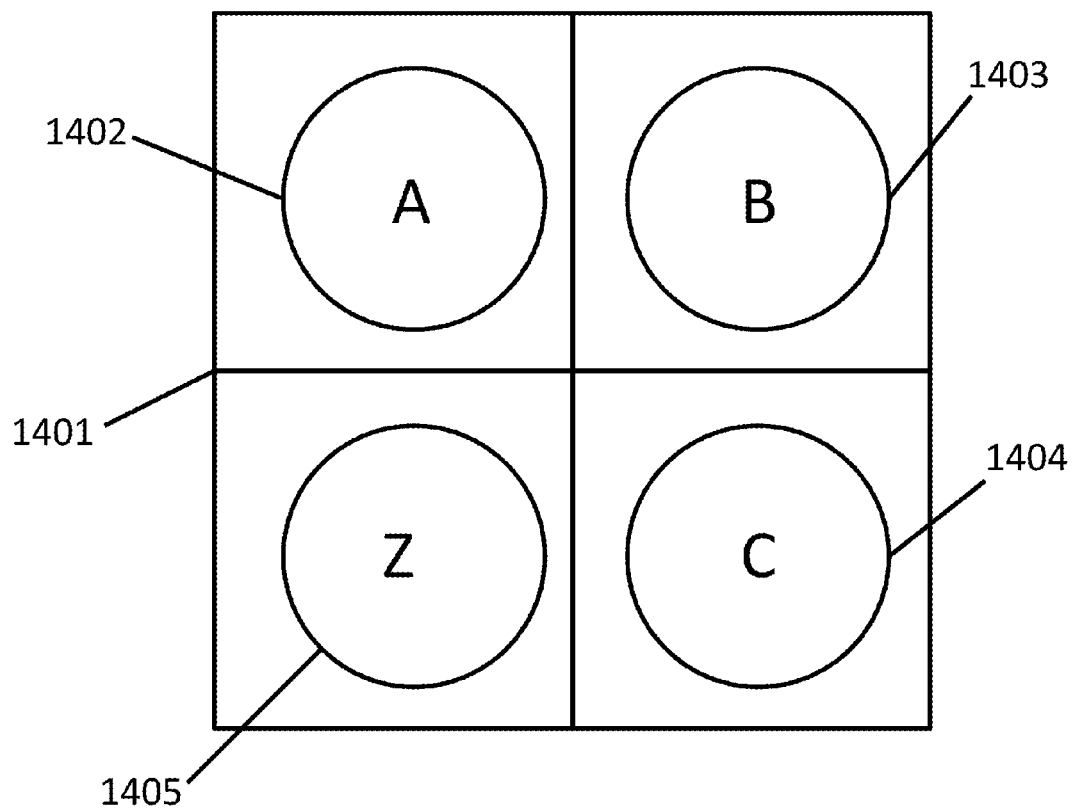
FIG. 14 provides a schematic example of discrete spots on a surface of a well, as described in Example 6.

A well comprising spots in the configuration of FIG. 14 is produced, using the methods described in this disclosure. With reference to FIG. 14, the bottom surface of a well 1401 is depicted. The shapes used for the well and the spots are merely for illustrative purposes and in no way meant to be limiting. Any suitable shape may be used for the well and/or any spot. With reference to FIG. 14, four spots are shown, each spot in one quadrant of the bottom surface of the well. The number of spots, and the contents of the spots, are also merely illustrative. Any number of spots or suitable contents of spots may be used. In FIG. 14, spot 1402 comprises a first modular component of a barcode (A), spot 1403 comprises a second modular component of a barcode (B), spot 1404 comprises a third modular component of a barcode (C), and spot 1405 comprises a reagent (Z). The spots are separated, to prevent mixing of the contents of the spots before a sample is added. By adding a sample (e.g., an analyte in a medium) to the well, the contents of the spots can be mixed with the sample at the appropriate time.

Example 7: Sonication of Encapsulated Polynucleotide

Polynucleotides (e.g., genomic DNA) are isolated from cells according to methods known in the art. The polynucleotides are encapsulated in a capsule and/or within a hydrogel matrix. The polynucleotides are fragmented by exposing the capsules and/or hydrogel matrix to shear stress induced by ultrasonic waves. Sheared, encapsulated polynucleotide is generated.

Figure 15A:
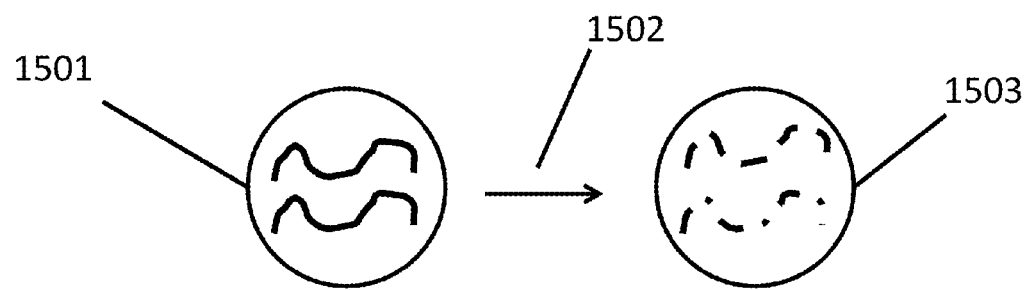
FIG. 15A-B provide schematic examples of shearing encapsulated DNA and exposing it to reagents for further processing, as described in Example 7.

With reference to FIG. 15A, a polynucleotide (e.g., isolated from a cell) is encapsulated in a capsule or a gel droplet 1501. As described elsewhere in this disclosure, the polynucleotide can be encapsulated such that each capsule or gel droplet comprises only a single copy of a particular polynucleotide, so that each capsule or gel droplet contains a mixture of non-overlapping fragments. The capsule or gel droplet is sonicated 1502 to shear the polynucleotide. The capsule or gel droplet is configured to withstand the sonication. The result is a capsule or gel droplet comprising fragmented polynucleotide 1503.

Figure 15B:
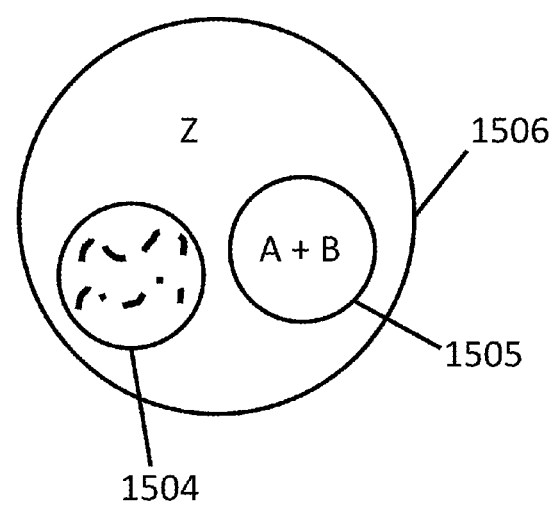

The encapsulated fragmented polynucleotide can then be processed according to any suitable method, including methods known in the art and methods described in this disclosure. FIG. 15B shows an example of further processing. With reference to FIG. 15B, the a first inner capsule or hydrogel droplet comprising sheared polynucleotides 1504 (as generated, e.g., in FIG. 15A) is encapsulated into an outer capsule 1506. The outer capsule 1506 also comprises a second inner capsule 1505. The second inner capsule 1505 comprises two modular components of a barcode (A+B). The medium between the outer capsule 1506 and the two inner capsules 1504 and 1505 comprises a reagent (Z). Upon releasing the contents of the inner capsules, the sheared polynucleotide will mix with A, B, and Z. In some cases, a plurality of capsules or hydrogel droplets comprising a sheared polynucleotide (i.e., a plurality of 1504s) may be encapsulated in the outer capsule 1506.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a plurality of capsules, said capsules situated within droplets in an emulsion, wherein said capsules are configured to release their contents into said droplets upon the application of a stimulus to provide said contents in said droplets in said emulsion, wherein said stimulus is selected from the group consisting of a change in pH, a change in ion concentration, reduction of disulfide bonds, and combinations thereof.

2. The composition of claim 1, wherein at least one of said capsules and said droplets comprise a species selected from the group consisting of a reagent and an analyte.

3. The composition of claim 2, wherein said reagent is selected from the group consisting of a protein, a polynucleotide, an enzyme, an antibody, a barcode, an adapter, a buffer, a small molecule, a detergent, a dye, a polymer and combinations thereof.

4. The composition of claim 3, wherein said enzyme is selected from the group consisting of a proteinase, a restriction enzyme, a ligase, a polymerase, a fragmentase, a reverse transcriptase, a transposase, and combinations thereof.

5. The composition of claim 4, wherein said restriction enzyme is a restriction enzyme that is a rare cutter.

6. The composition of claim 3, wherein said barcode is an oligonucleotide barcode.

7. The composition of claim 2, wherein said analyte is selected from the group consisting of a cell, a polynucleotide, a chromosome, a protein, a peptide, a polysaccharide, a sugar, a lipid, a small molecule, and combinations thereof.

8. The composition of claim 7, wherein said analyte is a polynucleotide.

9. The composition of claim 8, wherein said polynucleotide is selected from the group consisting of DNA, RNA, cDNA, and combinations thereof.

10. The composition of claim 8, wherein the amount of said polynucleotide in said composition is an amount sufficient to provide about 100-200X sequence coverage.

11. The composition of claim 7, wherein each capsule comprises, on average, about one chromosome.

12. The composition of claim 1, wherein each droplet comprises, on average, about 1 capsule per droplet.

13. The composition of claim 1, wherein each droplet can hold, at most, a single capsule.

14. The composition of claim 1, wherein at least one of said capsules comprises a further partition.

15. The composition of claim 14, wherein said further partition is selected from the group consisting of a capsule and a droplet in an emulsion.

16. The composition of claim 1, wherein at least one of said capsules has a shell selected from the group consisting of a polymeric shell, a hydrogel, a hydrophilic shell, a hydrophobic shell, a shell with a net positive charge, a shell with a net negative charge, a shell with a neutral charge, and combinations thereof.

17. The composition of claim 1, wherein said droplets comprise a fluid that is of a lesser density than the density of said capsules.

18. The composition of claim 1, wherein said droplets comprise a fluid that is of a greater density than the density of said capsules.

19. The composition of claim 1, wherein said capsules are produced by a method selected from the group consisting of emulsification polymerization, layer-by-layer assembly with polyelectrolytes, coacervation, internal phase separation, flow focusing, and combinations thereof.

20. The composition of claim 1, wherein said stimulus is applied to said capsules.

21. The composition of claim 1, wherein said stimulus is applied to said droplets.

22. A composition comprising a plurality of outer capsules in an emulsion, said outer capsules comprising at least one inner capsule, wherein said at least one inner capsule is configured to release its contents into at least one outer capsule among said plurality of outer capsules upon the application of a stimulus to provide said contents in said outer capsule in said emulsion, wherein said stimulus is selected from the group consisting of a change in pH, a change in ion concentration, reduction of disulfide bonds, and combinations thereof.

23. A device comprising a plurality of partitions, wherein at least one partition of said plurality of partitions comprises a capsule, wherein said capsule is situated within a droplet in an emulsion, wherein said capsule is configured to release its contents into said droplet upon the application of a stimulus to provide said contents in said droplet in said emulsion, wherein said stimulus is selected from the group consisting of a change in pH, a change in ion concentration, reduction of disulfide bonds, and combinations thereof.

24. A device comprising a plurality of partitions, wherein at least one partition of said plurality of partitions comprises an outer capsule in an emulsion, said outer capsule comprising at least one inner capsule, wherein said at least one inner capsule is configured to release its contents into said outer capsule upon the application of a stimulus to provide said contents in said outer capsule in said emulsion, wherein said stimulus is selected from the group consisting of a change in pH, a change in ion concentration, reduction of disulfide bonds, and combinations thereof.

25. A method comprising:
a. providing a plurality of capsules, said capsules situated within droplets in an emulsion, wherein said capsules are configured to release their contents into said droplets upon the application of a stimulus, wherein said stimulus is selected from the group consisting of a change in pH, a change in ion concentration, reduction of disulfide bonds, and combinations thereof; and
b. providing a stimulus to cause said capsules to release their contents into said droplets in said emulsion.

26. A method comprising:
a. providing a plurality of inner capsules, said inner capsules situated within outer capsules in an emulsion, wherein said inner capsules are configured to release their contents into said outer capsules upon the application of a stimulus, wherein said stimulus is selected from the group consisting of a change in pH, a change in ion concentration, reduction of disulfide bonds, and combinations thereof; and
b. providing a stimulus to cause said inner capsules to release their contents into said outer capsules in said emulsion.

27. The composition of claim 1, wherein said contents comprise at least 10,000 barcoded oligonucleotides releasably attached to each of said capsules.

28. The composition of claim 22, wherein said contents comprise at least 10,000 barcoded oligonucleotides releasably attached to said inner capsule.

29. The device of claim 23, wherein said contents comprise at least 10,000 barcoded oligonucleotides releasably attached to said capsule.

30. The device of claim 24, wherein said contents comprise at least 10,000 barcoded oligonucleotides releasably attached to said inner capsule.

31. The method of claim 25, wherein said contents comprise at least 10,000 barcoded oligonucleotides releasably attached to each of said capsule.

32. The method of claim 26, wherein said contents comprise at least 10,000 barcoded oligonucleotides releasably attached to each of said inner capsule.

33. The composition of claim 1, wherein said capsules are gels.

34. The composition of claim 22, wherein said inner capsule is a gel.

35. The composition of claim 22, wherein at least one of said inner capsules and said outer capsules comprise a species selected from the group consisting of a reagent and an analyte.

36. The composition of claim 35, wherein said reagent is selected from the group consisting of a protein, a polynucleotide, an enzyme, an antibody, a barcode, an adaptor, a buffer, a small molecule, a detergent, a dye, a polymer and combinations thereof.

37. The composition of claim 36, wherein said enzyme is selected from the group consisting of a proteinase, a restriction enzyme, a ligase, a polymerase, a fragmentase, a reverse transcriptase, a transposase, and combinations thereof.

38. The composition of claim 36, wherein said barcode is an oligonucleotide barcode.

39. The composition of claim 35, wherein said analyte is selected from the group consisting of a cell, a polynucleotide, a chromosome, a protein, a peptide, a polysaccharide, a sugar, a lipid, a small molecule, and combinations thereof.

40. The composition of claim 39, wherein said analyte is a polynucleotide.

* * * * *